(12) United States Patent
Chen et al.

(10) Patent No.: US 10,463,644 B2
(45) Date of Patent: Nov. 5, 2019

(54) USES OF SESQUITERPENE LACTONE COMPOUNDS AND THEIR DERIVATIVES IN DRUGS PREPARATION

(71) Applicants: ACCENDATECH, Tianjin (CN); NANKAI UNIVERSITY, Tianjin (CN)

(72) Inventors: Yue Chen, Tianjin (CN); Quan Zhang, Tianjin (CN); Jing Long, Tianjin (CN); Weiwei Ma, Tianjin (CN); Jiadai Zhai, Tianjin (CN); Xiudong Yang, Tianjin (CN); Hongxia Fan, Tianjin (CN); Yahui Ding, Tianjin (CN); Liang Wang, Tianjin (CN); Bin Han, Tianjin (CN); Xiaoyan Ma, Tianjin (CN); Haoliang Zhang, Tianjin (CN); Chuanjiang Qiu, Tianjin (CN)

(73) Assignees: ACCENDATECH, Tianjin (CN); NANKAI UNIVERSITY, Tianjin (CN)

( * ) Notice: Subject to any disclaimer, the term of this patent is extended or adjusted under 35 U.S.C. 154(b) by 260 days.

(21) Appl. No.: 15/110,592

(22) PCT Filed: Jul. 15, 2013

(86) PCT No.: PCT/CN2013/079344
§ 371 (c)(1),
(2) Date: Jul. 21, 2016

(87) PCT Pub. No.: WO2015/006893
PCT Pub. Date: Jan. 22, 2015

(65) Prior Publication Data
US 2016/0367525 A1    Dec. 22, 2016

(51) Int. Cl.
*A61K 31/365*    (2006.01)
*A61K 31/4025*    (2006.01)
*A61K 31/4192*    (2006.01)
*A61K 31/496*    (2006.01)
*A61K 31/4525*    (2006.01)
*A61K 31/5377*    (2006.01)

(52) U.S. Cl.
CPC ........ *A61K 31/365* (2013.01); *A61K 31/4025* (2013.01); *A61K 31/4192* (2013.01); *A61K 31/4525* (2013.01); *A61K 31/496* (2013.01); *A61K 31/5377* (2013.01)

(58) Field of Classification Search
CPC ..................................................... A61K 31/365
USPC ....................................................... 514/232.8
See application file for complete search history.

(56) References Cited

FOREIGN PATENT DOCUMENTS

CN          102731454       * 10/2012
WO      WO2011311103       * 10/2011

OTHER PUBLICATIONS

CN102731454 Machine English translation.*
Saklani et al. Phytomedicine (2012), vol. 19, pp. 988-997.*
Machine translation WO2011311103.*
Javab et al. (Arthritis (2012) vol. 2012, pp. 1-7 (Year: 2012).*
GenesCards PTGS2 [online] Retrieved on Jun. 6, 2018, [Retrieved from the internet], <url: https://www.genecards.org/cgi-bin/carddisp.pl?gene=PTGS2 (Year: 2009).*

* cited by examiner

*Primary Examiner* — Savitha M Rao
*Assistant Examiner* — Taina D Matos Negron
(74) *Attorney, Agent, or Firm* — JCIPRNET

(57) ABSTRACT

The present invention relates to the uses of sesquiterpene lactone compounds and their derivatives in preparing drugs. It belongs to the field of drug technology, specifically relates to the uses of the compounds of Formula (I) in preparing the drugs, especially the uses in preparing the drugs to treat rheumatoid arthritis and treat cancers through inhibiting cancer stem cells.

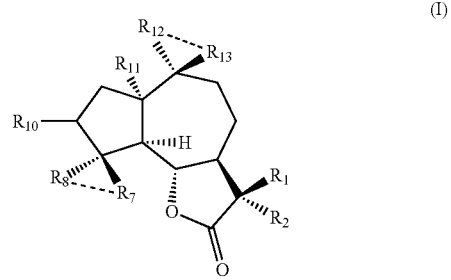

(I)

1 Claim, No Drawings

USES OF SESQUITERPENE LACTONE COMPOUNDS AND THEIR DERIVATIVES IN DRUGS PREPARATION

BACKGROUND OF THE INVENTION

Technical Field

The present invention belongs to the field of drug technology, specifically relates to the uses of sesquiterpene lactone compounds as the effective components or pharmaceutical composition in preparing drugs, especially the uses in preparing the drugs to treat rheumatoid arthritis and treat cancers through inhibiting cancer stem cells.

Description of Related Art

The rheumatoid arthritis (RA) is a chronic, inflammatory and systematic autoimmune disease. In addition, the tumors greatly threat the health of human. There are approximately two million of cancer patients in China currently and 1.6 million of cases are emerging every year, which is a rather huge number. RA is a progressive and multi-joint inflammatory systemic autoimmune disease, which mainly shows inflammatory hyperplasia of synovium, mononuclear cell infiltration and neovascularization. There is no therapeutic solution and preventive measures for radical cure of these diseases yet and the main drugs prescribed clinically include non-steroidal anti-inflammatory drugs and adrenal cortical hormones, etc. However, these drugs have severe side effects to result in damages to liver and kidney as well as pulmonary fibrosis. Therefore, it is difficult for the patients to adhere to long-term medication. Thus, our purpose is to find an effective and safe medicine for the treatment.

So far, there is no report concerning the application of the compounds of Formula (I) and their pharmaceutical compositions in preparing drugs to cure rheumatoid arthritis.

The tumors greatly threat the health of human. There are approximately two million of cancer patients in China currently and 1.6 million of cases are emerging every year, which is a rather huge number. Therefore, the anti-tumor research is a very challenging field, but with great significance to the present life science. The therapeutic methods in the past focus on eradicating and killing cancer cells and the anti-tumor drugs often used clinically are mainly cytotoxic agents so far. However, these anti-cancer drugs have the demerits such as poor selectivity, strong toxic side effects and tending to result in drug resistance, so they are typical double-sided drugs and it is difficult with them to eradicate cancer and a high ratio of some cancers tend to recur. High recurrence rate of malignant tumors is always a challenge annoying the oncologists. More and more studies have demonstrated that there are a small number of tumor stem cells in the tumor cell population, which can amplify the population. They are usually at the slow cycle state with low sensitivity to chemotherapy drugs and are the origins of tumor recurrence. Thus, the discovery of tumor stem cell provides a new target for tumor treatment and the drug research against tumor stem cell provides the possibility to completely heal cancer.

So far, there is no report concerning the application of the compounds of Formula (I) and their pharmaceutical compositions in treating cancer through inhibiting cancer stem cells.

BRIEF SUMMARY OF THE INVENTION

The present invention provides the uses of the compounds of Formula (I) in preparing drugs, especially the uses in preparing the drugs to treat rheumatoid arthritis and treat cancers through inhibiting cancer stem cells.

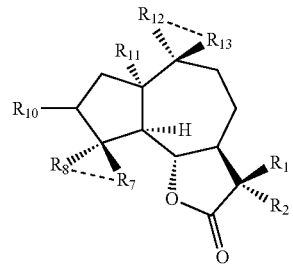

where: $R_1$ and $R_2$ form double bond together or $R_1$ is hydrogen or deuterium, $R_2$ is

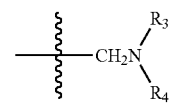

and the pharmaceutically acceptable salts formed by it and inorganic acid or organic acid, including the quaternary ammonium salts formed with $R_5Z$, $R_3$ and $R_4$ can be the same or different selected from hydrogen, alkyl,cycloalkyl, hydroxy-substituting alkyl, alkenyl, alkynyl, aryl, alkylaryl, arylalkyl, arylalkenyl, arylalkynyl, heterocyclic, trifluoromethyl, polyfluoroalkyl, nitrile group, cyanomethyl, acyl, carbamoyl, sulfonyl, sulfonamide or aryloxyalkyl. $R_3$, $R_4$ and N atom form cyclic structure which is preferably 3-member to 9-member ring, where one or more positions on the ring structure can be replaced by the substituent group including hydrogen, alkyl, cycloalkyl, alkenyl, alkynyl, aryl, alkylaryl, arylalkyl, arylalkenyl, arylalkynyl or heterocyclic; Z is fluorine, chlorine, bromine, iodine, toluene-p-sulfonate group, mesylate group, benzenesulfonate group or trifluoromethanesulfonate group. $R_5$ is alkyl, cycloalkyl, hydroxy-substituting alkyl, alkenyl, alkynyl, aryl, heterocyclic, aryl-substituting alkyl, arylalkenyl, arylalkynyl, cyano methyl, alkoxy-substituting alkyl or aryloxy substituting alkyl. Inorganic or organic acid can be hydrofluoric acid, hydrochloric acid, hydrobromic acid, hydroiodic acid, sulfuric acid, nitric acid, phosphoric acid, carbonic acid, boric acid, selenious acid, phosphomolybdic acid, phosphorous acid, sulfurous acid, citric acid, maleic acid, D-malic acid, L- malic acid, DL- malic acid, L- lactic acid, D- lactic acid, DL- lactic acid, oxalic acid, methanesulfonic acid, pentanoic acid, oleic acid, lauric acid, p-toluenesulfonic, 1-naphthalenesulfonic acid, 2-naphthalenesulfonic acid, phthalic acid, tartaric acid, malonic acid, succinic acid, fumaric acid, glycolic acid, a thiol acid, glycine, sarcosine, sulfonic acid, nicotinic acid, picoline acid, isonicotinic, dichloroacetic acid, benzoic acid or substituted benzoic acid. Or $R_2$ is

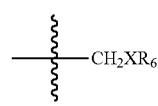

where X thereof is O or S, $R_6$ is hydrogen, alkyl, cycloalkyl, hydroxy-substituting alkyl, alkenyl, alkynyl, aryl, alkylaryl, arylalkyl, arylalkenyl, arylalkynylp, heterocyclic, trifluoromethyl, polyfluoroalkyl, nitrile group, cyanomethyl, acyl, carbamoyl, sulfonyl, sulfonamide or aryloxyalkyl.

If there is no bond - - - between $R_7$ and $R_8$, $R_7$ and $R_8$ will form double bond together or $R_7$ is methyl, $R_8$ is hydroxyl or $OCOR_9$, where $R_9$ thereof is alkyl, substituted alkyl, alkenyl, substituted alkenyl, aryl, substituted aryl, heterocyclic, substituted heterocyclic.

If the bond - - - between $R_7$ and $R_8$ is single bond, $R_7=R_8=$methylene.

$R_{10}$ is hydrogen or $R_{10}$ and $R_8$ form single bond.

$R_{11}$ is hydrogen or $R_{11}$ and $R_{13}$ form single bond or epoxy bond.

If these is no bond - - - between $R_{12}$ and $R_{13}$, $R_{12}$ and $R_{13}$ will form double bond together or $R_{12}$ is hydroxyl or $OR_{14}$, where $R_{14}$ thereof is alkyl, substituted alkyl, alkenyl, substituted alkenyl, aryl, substituted aryl, heterocyclic, substituted heterocyclic, $R_{13}$ is methyl.

If the bond - - - between $R_{12}$ and $R_{13}$ is single bond, $R_{12}=R_{13}=$methylene.

The structural formula (I) is preferably.

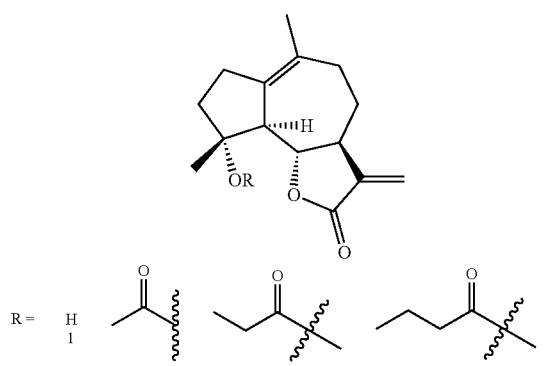

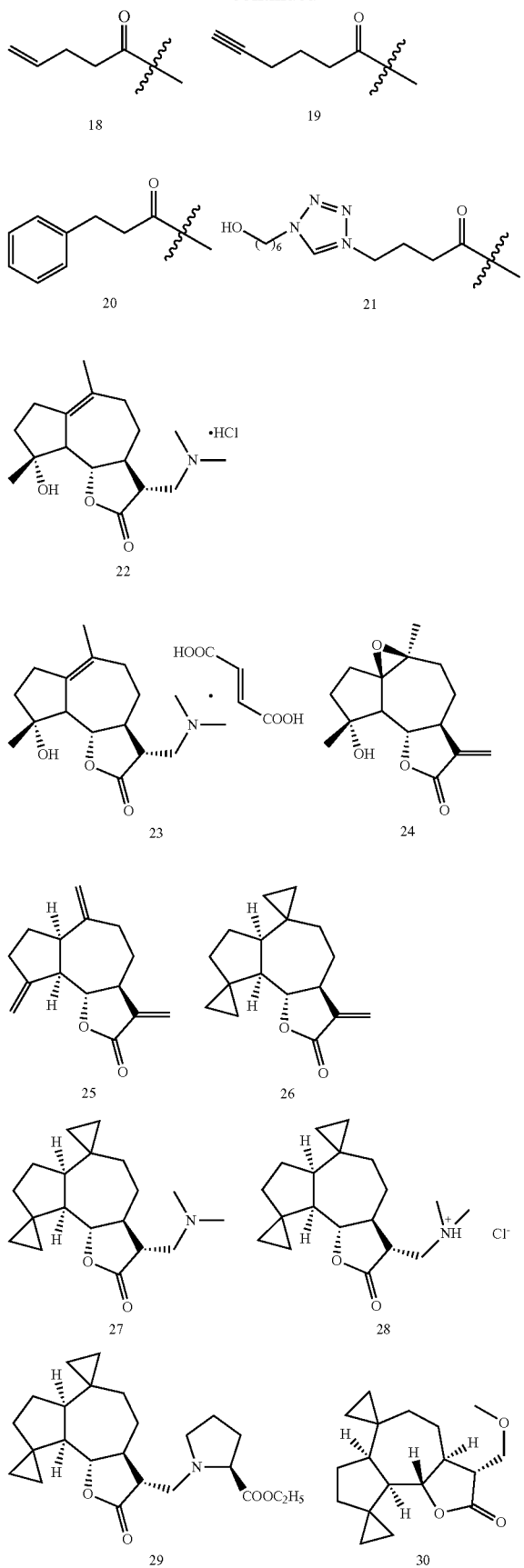

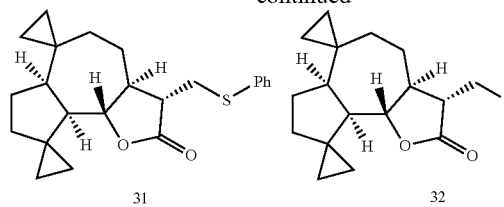
31 32
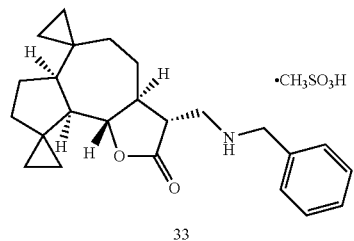
33
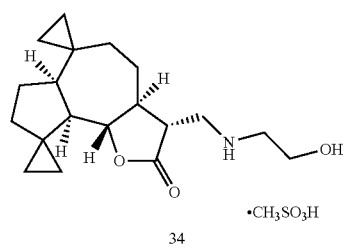
34
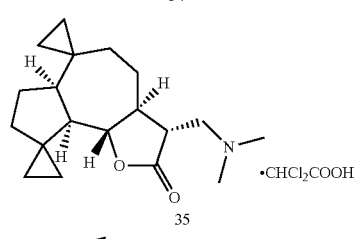
35
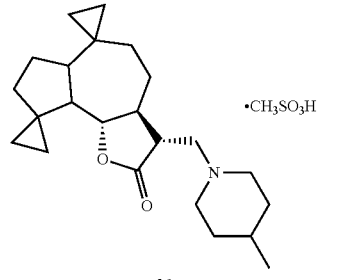
36
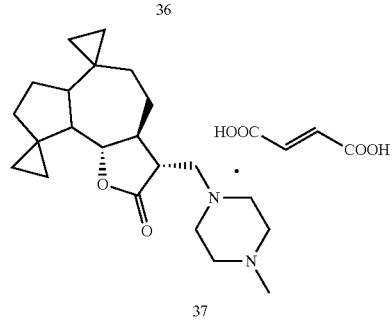
37
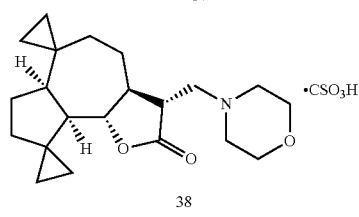
38
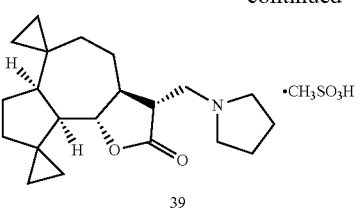
39
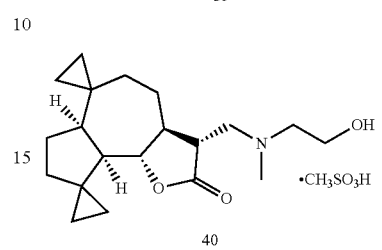
40
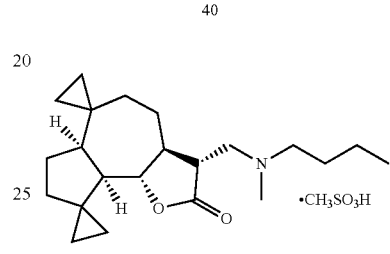
41
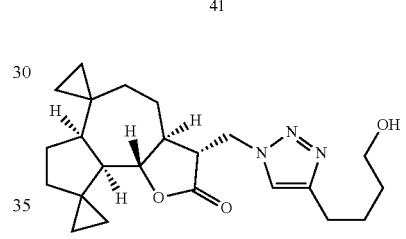
42
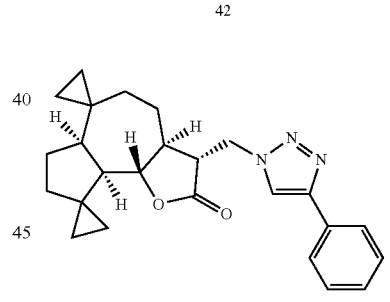
43
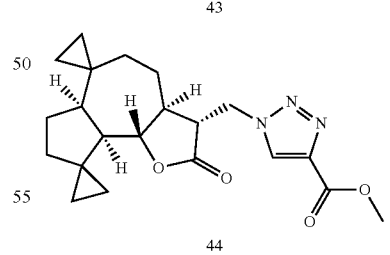
44
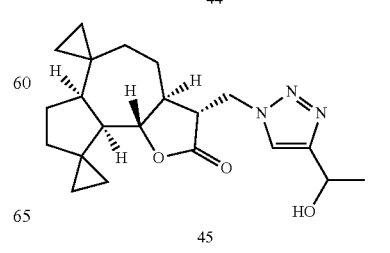
45

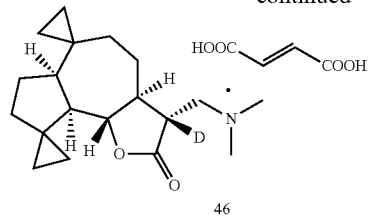

46

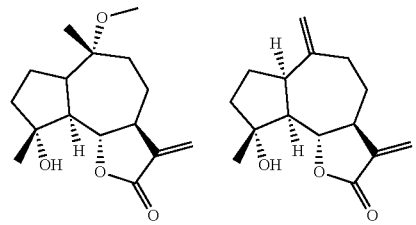

47  48

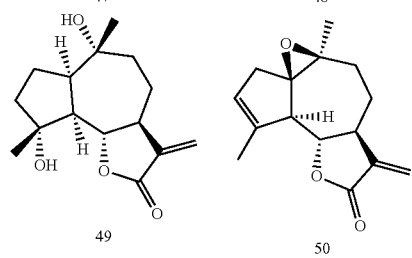

49  50

The uses of the above-mentioned compounds in preparing the drugs to treat rheumatoid arthritis.

The uses of the above-mentioned compounds in preparing the adjuvant drugs to treat rheumatoid arthritis.

The uses of the above-mentioned compounds in preparing the drugs to treat cancers through inhibiting cancer stem cells, where the cancers thereof are preferably acute myeloid leukemia, chronic myeloid leukemia, chronic lymphocytic leukemia, skin cancer, breast cancer, ovarian cancer, brain tumor, prostate cancer, head and neck squamous cell carcinoma, laryngeal cancer, pancreatic cancer, retinoblastoma, children hepatoblastoma, liver cancer, malignant melanoma, colorectal cancer, colon cancer, glioma, gastrointestinal tumor, nasopharyngeal carcinoma, brain glioma, gastric cancer, lung adenocarcinoma and lung cancer.

The uses of the above-mentioned compounds in preparing the adjuvant drugs to treat cancers through inhibiting cancer stem cells, where the cancers thereof are preferably acute myeloid leukemia, chronic myeloid leukemia, chronic lymphocytic leukemia, skin cancer, breast cancer, ovarian cancer, brain tumor, prostate cancer, head and neck squamous cell carcinoma, laryngeal cancer, pancreatic cancer, retinoblastoma, children hepatoblastoma, liver cancer, malignant melanoma, colorectal cancer, colon cancer, glioma, gastrointestinal tumor, nasopharyngeal carcinoma, brain glioma, gastric cancer, lung adenocarcinoma and lung cancer.

The present invention also provides a pharmaceutical composition comprising at least one compound according to any claim of claim 1 to claim 2 as the active component and a pharmaceutically acceptable carrier or other compound(s) to treat rheumatoid arthritis.

The present invention also provides a pharmaceutical composition comprising at least one compound according to any claim of claim 1 to claim 2 as the active component and a pharmaceutically acceptable carrier or other compound(s) to treat cancer.

If the compounds according to the present invention are used as drugs, they can be directly used or in the form of pharmaceutical composition. This pharmaceutical composition comprises the compound according to the present invention with a content of 0.1-99%, preferably 0.5-90% and other pharmaceutical carrier and/or excipient which is pharmaceutically acceptable, nontoxic to human and animal and inert, or is a drug combination with other drug(s) to treat rheumatoid arthritis. The composition according to the present invention can be prepared into the form of injection, tablet or capsule, etc.

Said pharmaceutical carrier or excipient is one or more solids, semi-solids and liquid diluents, fillers and pharmaceutical adjuvants. The pharmaceutical composition according to the present invention is used in the form of dose per unit body weight. The drugs according to the present invention can be delivered in two forms as injection and oral administration, for example, the former can be intravenous and intramuscular injection and the dosage form of the latter can be tablet and capsule.

DETAILED DESCRIPTION OF THE INVENTION

In order to understand the present invention, the following embodiments are used to further describe the present invention. Nevertheless, it is not to limit the protection scope of the present invention.

Embodiment 1: Preparation Method of Compound 1-50

Preparation of Compound 1:

Dissolve the parthenolide (50 mg, 02 mmol) in 2.5 mL $CH_2Cl_2$ and add p-toluenesulfonic acid (5 mg, 0.026 mmol). Place the reaction system at room temperature and stir it overnight. Transfer the reaction solution into the saturated solution of $NaHCO_3$ (10 mL), collect the organic phase and extract the aqueous phase with a small amount of $CH_2Cl_2$, then mix the organic phases together and dry with $Na_2SO_4$ before filtering it. Distill the organic solvent at reduced temperature with rotary evaporator, then purify it with silica gel column to get Compound 1 (45 mg, yield is 90%). $^1H$ NMR ($CDCl_3$, 400 MHz) δ 6.20 (d, J=3.2 Hz, 1H) 5.49 (d, J=32 Hz, 1H) 3.81 (t, J=10.4 Hz, 1H), 270 (d, J=10.4 Hz, 1H), 2.65-2.62 (m, 2H), 2.40-2.34 (m, 1H), 2.07-2.26 (m, 4H), 1.73-1.86 (m, 2H), 1.68 (s, 3H), 1.36-1.28 (m, 4H); $^{13}C$ NMR ($CDCl_3$, 100 MHz) δ 169.8, 138.7, 131.7, 130.8, 119.5, 84.1, 80.2, 58.5, 49.5, 382, 34.8, 30.0, 25.7, 23.9, 23.6.

Common Preparation Method of Compounds 2-20:

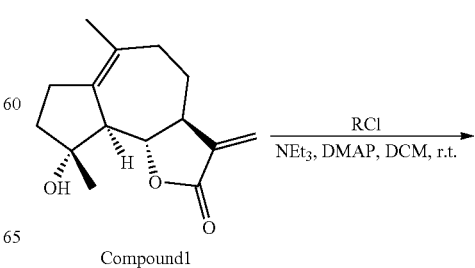

Compound1

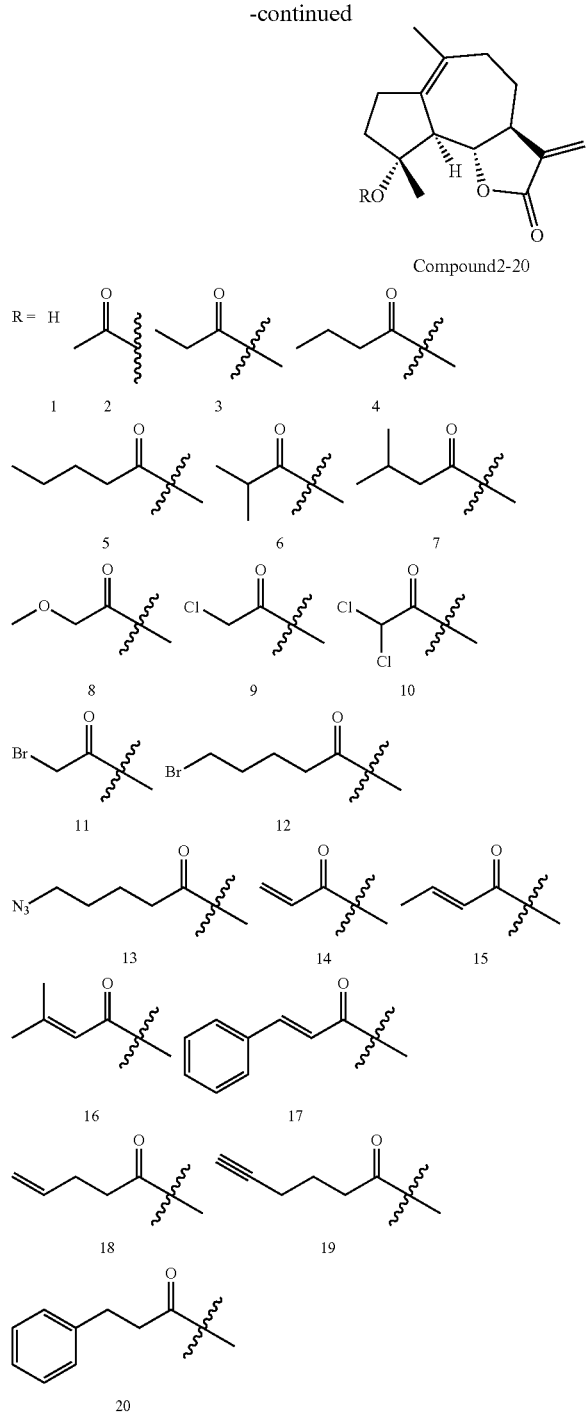

Compound 2-20

Under the protection by nitrogen gas and in ice-water bath, drip the acyl chloride (RCl) into the mixture of Compound 1 (24.8 mg, 0.1 mmol, DMAP (1.25 mg, 0.01 mmol) and trimethylamine (0.12 mL, 12 mmol), once the dripping ends, remove the ice-water bath and stir the system at room temperature until TLC test confirms the reaction ends. Pour the reaction mixture into ice water and extract with ethyl acetate (5 mL×3), wash the organic layer with citric acid solution (20 mL), saturated NaHCO$_3$ (10 mL) and saturated saline solution (10 mL) in turn. Dry the organic phase with anhydrous sodium sulfate and concentrate it under reduced pressure to yield the crude product, then separate it with silica gel column chromatography to get pure product.

The yield of Compound 2 is 62.8%. $^1$H NMR(400 MHz, CDCl$_3$z)δ 6.13(1H, d, J=3.1 Hz), 5.40(1H, d, J=2.8 Hz) 3.72(1H, t, J=10.2 Hz) 3.08(1H, d, J=10.1 Hz) 2.65~2.59 (1H, m) 2.41~2.35(2H, m), 2.21~2.13(4H, m), 2.04~2.00 (1H, m), 1.97(3H, s), 1.91~1.83(1H, m), 1.65(3H, s), 1.48 (3H, s); $^{13}$C NMR(100 MHz, CDCl$_3$)δ 169.6, 169.3, 138.4, 130.6, 129.4, 117.8, 87.7, 82.0, 55.6, 49.1, 35.4, 33.9, 29.4, 24.9, 232, 21.5, 17.8.

The yield of Compound 3 is 70.0%, $^1$H NMR (400 MHz, CDCl3) δ6.20 (1H, d, J=3.1 Hz), 5.47 (1H, d, J=2.8 Hz), 3.79 (1H, t, J=10.1 Hz), 3.13 (1H, d, J=10.2 Hz), 2.71~2.66 (1H, m), 2.49~2.42 (2H, m), 2.38~2.30 (2H, m), 2.28~2.26 (4H, m), 2.11~2.08 (1H, dd, J=13.8, 1.8 Hz), 1.97~1.89 (1H, m), 1.72 (3H, s), 1.57 (6H, d, J=9.0 Hz); $^{13}$C NMR (100 MHz, CDCl3) δ173.8, 170.2, 139.5, 131.5, 130.4, 118.6, 88.4, 83.0, 56.6, 50.1, 36.5, 34.9, 30.4, 28.7, 25.9, 24.1, 18.8, 9.1.

The yield of Compound 4 is 30.0%, $^1$H NMR (400 MHz, CDCl3)δ6.22 (1H, d, J=2.7 Hz), 5.49 (1H, d, J=2.1 Hz), 3.81 (1H, t, J=10.1 Hz), 3.16 (1H, d, J=103 Hz), 2.52~2.44 (2H, m), 236~2.23 (6H, m), 2.13~2.10 (1H, m), 1.99~1.91 (1H, m), 1.74 (3H, s), 1.70~1.68 (1H, m), 1.65 (3H, s), 1.57 (2H, s), 0.98 (3H, t, J=73 Hz); $^{13}$C NMR (100 MHz, CDCl3) δ173.2, 170.3, 139.5, 131.6, 130.5, 118.7, 88.5, 83.0, 56.8, 50.2, 37.4, 36.6, 35.0, 30.5, 25.9, 242, 18.8, 18.5, 13.6.

The yield of Compound 5 is 37.6%, $^1$H NMR (400 MHz, CDCl3) δ6.19 (1, d, J=3.1 Hz), 5.47 (1H, d, J=2.9 Hz), 3.78 (1H, t, J=10.1 Hz), 3.13 (1H, d, J=10.0 Hz), 2.72~2.66 (1H, m), 2.49~2.42 (2H, m), 2.37~2.31 (1H, m), 2.30~2.26 (4H, m), 2.12~2.08 (1H, dd, J=13.7, 2.2 Hz), 1.97~1.88 (1H, m), 1.75 (3H, s), 1.64~1.56 (2H, m), 1.55 (3H, s), 1.40~131 (3H, m), 0.92 (3H, t, J=73 Hz); $^{13}$C NMR (100 MHz, CDCl3) δ173.4, 1702, 139.5, 131.6, 130.4, 118.7, 88.5, 83.0, 56.8, 50.2, 36.5, 352, 34.9, 30.5, 27.1, 25.9, 24.1, 222, 18.8, 13.8.

The yield of Compound 6 is 26.8%, $^1$H NMR (400 MHz, CDCl3) δ6.21 (1H, d, J=3.0 Hz), 5.48 (1H, d, J=2.8 Hz), 3.81 (1H, t, J=10.1 Hz), 3.15 (1H, d, J=10.3 Hz), 2.74~2.68 (1H, m), 2.57~2.44 (3H, m), 2.30~229 (3H, m), 2.14~2.10 (1H, dd, J=13.7, 2.1 Hz), 1.98~1.90 (1H, m), 1.74 (3H, s), 1.66 (1H, s), 1.56 (3H, s), 1.21~1.17 (6H, m); $^{13}$C NMR (100 MHz, CDCl3) δ176.6, 170.2, 139.6, 131.5, 130.4, 118.6, 882, 83.0, 56.8, 50.1, 36.5, 35.0, 34.7, 30.5, 26.0, 24.2, 19.0, 18.9, 18.7.

The yield of Compound 7 is 47.8% $^1$H NMR (400 MHz, CDCl3) δ6.19 (1H, d, J=3.2 Hz), 5.46 (1H, d, J=2.9 Hz), 3.78 (1H, t, J=10.1 Hz), 3.13 (1H, d, J=10.1 Hz), 2.71~2.66 (1H, m), 2.50~2.42 (2H, m), 2.28~2.26 (3H, m), 2.20~2.07 (4H, m), 1.97~1.89 (1H, m), 1.72~1.69 (4H, m), 1.56 (3H, s), 0.97 (6H, d, J=5.9 Hz); $^{13}$C NMR (100 MHz, CDCl3) δ172.7, 170.2, 139.5, 131.6, 130.5, 118.7, 88.5, 83.0, 56.8, 502, 44.6, 36.6, 35.0, 30.5, 25.9, 25.8, 24.2, 22.4, 22.3, 18.8.

The yield of Compound 8 is 13.9% $^1$H NMR (400 MHz, CDCl3) δ6.20 (1H, d, J=2.9 Hz), 5.47 (1H, d, J=2.4 Hz), 4.07~3.95 (2H, q, J=16.4 Hz), 3.79 (1H, t, J=10.1 Hz), 3.47 (3H, s), 3.19 (1H, d, J=10.1 Hz), 2.71~2.66 (1H, m), 2.51~2.44 (2H, m), 2.27 (3H, s), 2.11~2.08 (1H, dd, J=12.5, 0.7 Hz), 2.04~1.95 (1H, m), 1.72 (3H, s) 1.63 (1H, s), 1.58 (3H, s); $^{13}$C NMR (100 MHz, CDCl3) δ170.2, 169.7, 139.3, 131.9, 130.0, 118.9, 89.6, 82.9, 70.3, 59.3, 56.4, 50.0, 36.4, 35.0, 30.4, 25.9, 242, 18.9.

The yield of Compound 9 is 56.2%, $^1$H NMR (400 MHz, CDCl3) δ6.23 (1H, d, J=33 Hz), 5.50 (1H, d, J=3.1 Hz), 4.14~4.05 (2H, m), 3.81 (1H, t, J=10.1 Hz), 3.20 (1H, d, J=10.0 Hz), 2.74~2.68 (1H, m), 2.54~2.47 (2H, m), 2.30~2.29 (3H, m), 2.15~2.11 (1H, dd, J=13.8, 2.3 Hz), 2.07~1.97 (1H, m), 1.75 (3H, s), 1.62 (4H, s); $^{13}$C NMR (100 MHz, CDCl3) δ170.1, 166.4, 139.2, 132.1, 129.8, 119.0, 90.8, 82.8, 56.4, 50.1, 42.0, 363, 35.0, 303, 25.9, 242, 18.8.

The yield of Compound 10 is 20.7%, $^{1}$H NMR (400 MHz, CDCl3) δ6.23 (1H, d, J=3.3 Hz), 5.96 (1H, s), 5.51 (1H, d, J=3.0 Hz), 3.81 (1H, t, J=10.1 Hz), 3.21 (1H, d, J=10.1 Hz), 2.76~2.70 (1H, m), 2.56~2.48 (2H, m), 2.30 (3H, s), 2.15~2.11 (1H, dd, J=13.8, 2.3 Hz), 2.07~1.99 (1H, m), 1.75 (3H, s), 1.66 (4H, s); $^{13}$C NMR (100 MHz, CDCl3) δ169.9, 163.4, 139.2, 132.4, 129.5, 119.0, 923, 82.5, 65.2, 56.5, 50.1, 36.0, 34.9, 302, 25.9, 24.1, 18.6.

The yield of Compound 11 is 46.5% $^{1}$H NMR (400 MHz, CDCl3) δ6.22 (1H, d, J=3.3 Hz), 5.49 (1H, d, J=3.0 Hz), 3.86 (2H, s), 3.80 (1H, J=10.1 Hz), 3.18 (1H, d, J=9.9 Hz), 2.74~2.68 (1H, m), 2.53~2.46 (2H, m), 230~2.29 (3H, m), 2.14~2.10 (1H, dd, J=13.8, 2.3 Hz), 2.06~1.94 (1H, m), 1.74 (3H, s), 1.71 (1H, s), 1.60 (3H, s); $^{13}$C NMR (100 MHz, CDCl3) δ170.1, 166.3, 139.3, 132.1, 129.9, 118.9, 90.8, 82.8, 56.5, 50.1, 36.2, 34.9, 303, 27.7, 25.9, 24.2, 18.7.

The yield of Compound 12 is 25.8% $^{1}$H NMR (400 MHz, CDCl3) δ6.22 (1H, d, J=3.2 Hz), 5.49 (1H, d, J=2.8 Hz), 3.81 (1H, t, J=102 Hz), 3.47 (2H, t, J=6.5 Hz), 3.15 (1H, d, J=10.0 Hz), 2.73~2.68 (1H, m), 2.51~2.44 (2H, m), 2.40~2.32 (2H, m), 2.30 (2H, d, J=6.4 Hz), 2.14~2.10 (1H, dd, J=13.7, 1.9 Hz), 1.99~1.91 (3H, m), 1.83~1.78 (2H, m), 1.74 (3H, s), 1.60 (3H, s), 1.57 (2H, s); $^{13}$C NMR (100 MHz, CDCl3) δ172.5, 170.2, 139.4, 131.7, 130.2, 118.8, 88.75, 83.0, 56.7, 50.1, 36.5, 35.0, 34.5, 33.5, 32.0, 30.5, 25.9, 24.2, 23.6, 18.8.

The yield of Compound 13 is 47.6% $^{1}$H NMR (400 MHz, CDCl3) δ6.22 (1H, d, J=3.3 Hz), 5.49 (1H, d, J=3.0 Hz), 3.81 (1H, t, J=102 Hz), 3.37~3.33 (2H, m), 3.16 (1H, d, J=10.1 Hz), 2.74~2.68 (1H, m), 2.51~2.45 (2H, m), 2.41~233 (2H, m), 2.31~2.29 (3H, m), 2.14~2.10 (1H, dd, J=13.7, 2.2 Hz), 2.00~1.92 (1H, m), 1.74 (3H, s), 1.73~1.66 (4H, m), 1.62 (1H, s), 1.57 (3H, s); $^{13}$C NMR (100 MHz, CDCl3) δ171.5, 169.2, 138.4, 130.7, 129.2, 117,7, 87.7, 82.0, 55.7, 50.1, 49.1, 35.5, 34.0, 33.9, 29.4, 272, 24.9, 23.1, 212, 17.8.

The yield of Compound 14 is 78.2%, $^{1}$H NMR (400 MHz, CDCl3) δ6.47~6.37 (1H, dd, J=17.3, 1.3 Hz), 6.21 (1H, d, J=33 Hz), 6.13~6.06 (1H, m), 5.80~5.77 (1H, dd, J=10.3, 1.3 Hz), 5.48 (1H, d, J=3.1 Hz), 3.82 (1H, J=10.1 Hz), 3.15 (1H, d, J=10.1 Hz), 2.73~2.67 (1H, m), 2.58~2.44 (2H, m), 2.29~2.27 (3H, m), 2.12~2.08 (1H, d, J=13.7, 2.3 Hz), 2.00~1.92 (1H, m), 1.73 (3H, s), 1.59 (4H, s); $^{13}$C NMR (100 MHz, CDCl3) δ170.3, 165.5, 139.4, 131.7, 130.2, 130.1, 130.0, 118.8, 88.8, 83.0, 57.1, 50.1, 36.5, 35.0, 30.5, 25.9, 242, 18.6.

The yield of Compound 15 is 13.5%, $^{1}$H NMR (400 MHz, CDCl3) δ6.22 (1H, d, J=3.3 Hz), 5.49 (1H, d, J=3.0 Hz), 5.20 (1H, d, J=5.0 Hz), 5.16 (1H, s), 3.81 (1H, t, J=10.1 Hz), 3.16 (1H, d, J=8.8 Hz), 3.12~3.09 (2H, m), 2.74~2.68 (1H, m), 2.51~2.44 (2H, m), 230~2.28 (4H, m), 2.14~2.10 (1H, dd, J=13.7, 2.1 Hz), 2.00~1.92 (1H, m), 1.88~1.86 (1H, dd, J=6.9, 1.3 Hz), 1.74 (3H, s), 1.59 (1H, s), 1.58 (3H, s); $^{13}$C NMR (100 MHz, CDCl3) δ171.0, 170.2, 139.5, 131.7, 130.7, 1303, 118.7, 118.2, 89.0, 83.0, 56.7, 50.1, 402, 36.5, 35.0, 30.5, 25.9, 24.2, 18.8.

The yield of Compound 16 is 26.6%, $^{1}$H NMR (400 MHz, CDCl3) δ6.20 (1H, d, J=3.2 Hz), 5.68 (1H, s), 5.47 (H, d, J=2.8 Hz), 3.81 (1H, t, J=10.2 Hz), 3.15 (1H, d, J=10.0 Hz), 2.73~2.67 (1H, m), 2.57~2.43 (2H, m), 2.28~2.27 (3H, m), 2.15 (3H, s), 2.12~2.08 (1H, d, J=13.9, 2.1 Hz), 2.00~1.92 (2H, m), 1.87 (3H, m), 1.73 (3H, s), 1.59 (3H, s); $^{13}$C NMR (100 MHz, CDCl3) δ170.3, 166.2, 155.4, 139.5, 131.5, 130.6, 118.7, 117.7, 882, 83.1, 57.0, 503, 36.8, 34.9, 30.6, 27.4, 25.9, 242, 20.1, 18.9.

The yield of Compound 17 is 23.3%, $^{1}$H NMR (400 MHz, CDCl3) δ7.76 (1H, d, J=16.0 Hz), 7.59~7.57 (2H, m), 7.39 (3H, d, J=5.0 Hz), 6.45 (1H, d, J=16.0 Hz), 6.24 (1H, d, J=3.1 Hz), 5.51 (1H, d, J=2.7 Hz), 3.88 (1H, t, J=10.2 Hz), 3.20 (1H, d, J=10.0 Hz), 2.78~2.73 (1H, m), 2.65~2.61 (1H, m), 2.55~2.48 (1H, m), 2.31 (3H, s), 2.16 (1H, d, J=13.5 Hz), 2.07~1.98 (1H, q), 1.75 (3H, s), 1.63 (4H, s); $^{13}$C NMR (100 MHz, CDCl3) δ170.4, 166.4, 144.5, 139.5, 134.7, 131.6, 130.0, 129.9, 128.8, 128.2, 119.7, 118.8, 88.7, 83.1, 573, 50.0, 36.7, 35.0, 30.6, 26.0, 24.2, 18.6.

The yield of Compound 18 is 53.3% $^{1}$H NMR (400 MHz, CDCl3) δ 6.18 (1H, d, J=3.2 Hz), 5.87~5.80 (1H, m), 5.46 (1H, d, J=3.0 Hz), 5.09 (1H, d, J=16.9 Hz), 5.00 (1H, d, J=9.6 Hz), 3.80~3.74 (1H, m), 3.12 (1H, d, J=7.4 Hz), 2.68 (1H, s), 2.45~2.40 (3H, m), 2.37 (4H, s), 2.25 (3H, s), 2.11~2.07 (1H, m), 1,95~1.89 (1H, m), 1.71 (3H, s), 1.54 (3H, d, J=3.8 Hz): $^{13}$C NMR (100 MHz, CDCl3) δ172.4, 170.2, 139.5, 136.9, 131.6, 1303, 118.7, 1153, 88.7, 82.9, 56.7, 50.1, 36.5, 35.0, 34.6, 30.4, 29.0, 25.9, 24.2, 18.8.

The yield of Compound 19 is 65.2%, $^{1}$H NMR (400 MHz, CDCl3) δ6.21 (1H, d, J=3.1 Hz), 5.49 (1H, d, J=2.7 Hz), 3.82 (1H, t, J=10.0 Hz), 3.15 (1H, d, J=93 Hz), 2.91~2.82 (3H, m), 2.14~2.10 (1H, m), 2.04~2.01 (3H, m), 1.97~1.87 (8H, m), 1.83~1.75 (6H, m), 1.63 (1H, s); $^{13}$C NMR (100 MHz, CDCl3) δ172.4, 170.2, 139.4, 131.7, 130.2, 118.8, 88.8, 83.6, 83.0, 69.0, 56.7, 50.1, 36.5, 34.9, 34.1, 30.5, 25.9, 242, 23.7, 18.8, 17.8.

The yield of Compound 20 is 24.0%, $^{1}$H NMR (400 MHz, CDCl3) δ7.32~7.18 (5H, m), 6.22 (1H, d, J=33 Hz), 5.49 (1H, d, J=3.0 Hz), 3.80 (1H, t, J=10.1 Hz), 3.12 (1H, d, J=10.1 Hz), 2.99 (2H, t, J=7.9 Hz), 2.73~2.59 (3H, m), 2.49~2.43 (2H, m), 230~2.28 (3H, m), 2.14~2.10 (1H, dd, J=13.8, 2.3 Hz), 1.96~1.87 (1H, m), 1.74 (3H, s), 1.65 (1H, s), 1.56 (3H, s): $^{13}$C NMR (100 MHz, CDCl3) δ172.3, 170.2, 140.8, 139.5, 131.6, 130.4, 128.4, 126.0, 118.7, 88.8, 83.0, 56.7, 50.1, 36.8, 36.5, 35.0, 31.0, 30.5, 26.0, 24.2, 18.8.

Synthesis of Compound 21:

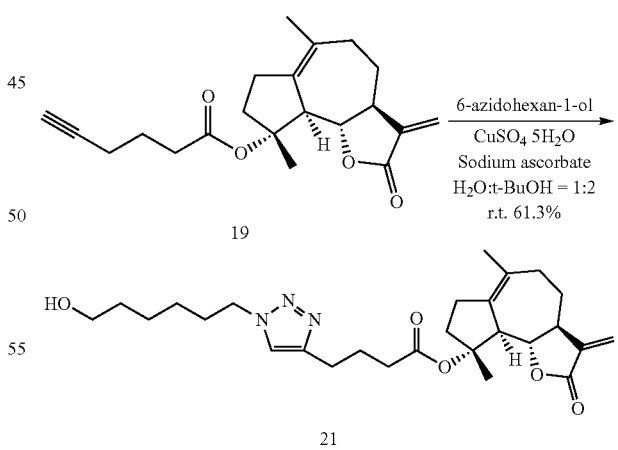

In one dry and clean reaction flask of 10 mL, add 5-acetylenic acid and Compound 19 (200 mg, 0.584 mmol), 6-azido-1-n-hexanol (125.43 mg, 0.876 mmol), copper sulfate hydrate (145.80 mg, 0.584 mmol) and sodium ascorbate (462.78 mg, 2.336 mmol), then add the mixture solution of distilled water and tert-butyl alcohol (1:2) (3 mL) to dissolve them to homogeneous phase and then stir it for 2 hours at room temperature. Remove partial solvent with rotary evaporator and extract the remaining reaction solution mixture with ethyl acetate, then collect the organic phase and dry with anhydrous sodium sulfate and filter at reduced pressure. Dry the organic phase with rotary evaporator and separate it with silica column chromatography to get Compound 21 (120.0 mg) with a yield of 61.3%. $^1$H NMR (400 MHz, CDCl3) δ7.52 (1H, s), 6.20 (1H, d, J=3.3 Hz), 5.49 (1H, d, J=3.0 Hz), 4.34 (2H, t, J=7.1 Hz), 3.81 (1H, t, J=10.2 Hz), 3.63 (2H, t, J=6.4 Hz), 3.14 (1H, d, J=10.1 Hz), 2.81~2.76 (2H, m), 2.74~2.67 (1H, m), 2.51~2.43 (2H, m), 239~231 (2H, m), 2.29~2.27 (4H, m), 2.13~2.09 (1H, dd, J=13.8, 2.3 Hz), 2.05~2.00 (3H, m), 1.97~1.88 (5H, m), 1.72 (4H, s), 1.60~1.53 (6H, m); $^{13}$C NMR (100 MHz, CDCl3) δ172.6, 170.2, 147.1, 139.4, 131.7, 130.0, 1213, 118.8, 88.6, 83.1, 622, 56.7, 50.0, 49.9, 36.4, 34.9, 34.7, 32.3, 30.4, 30.1, 26.1, 25.8, 25.1, 24.8, 24.7, 24.1, 18.8.

Preparation of Compound 22:

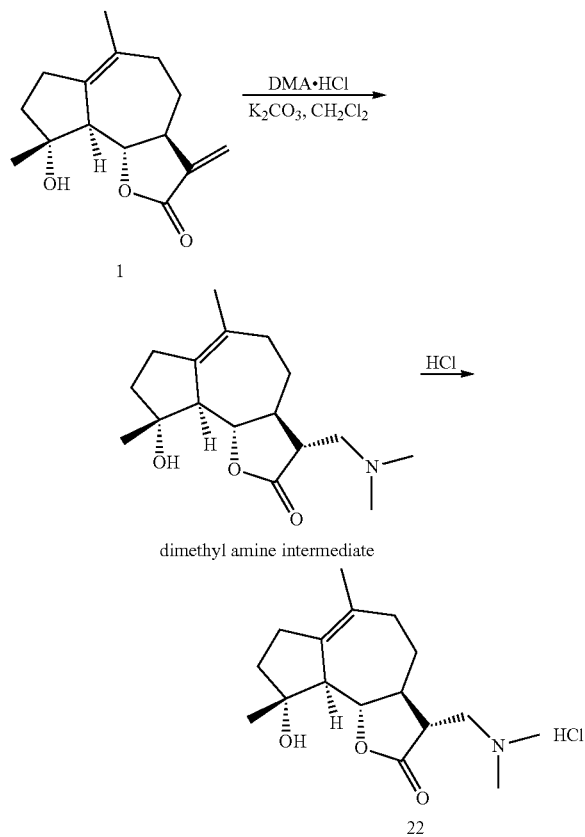

Mix dimethylamine hydrochloride (1.5 g, 18 mmol) and K$_2$CO$_3$ (5.0 g, 36 mmol) and then add them into 100 ml CH$_2$Cl$_2$ to stir 15 minutes, then filter under pressure and directly add into Compound 5 (300 mg, 12 mmol) and stir for 3 h at room temperature. Remove the solvent at reduced pressure and dissolve it with a few amount of CH$_2$Cl$_2$, wash it three times rapidly with water and dry with Na$_2$SO$_4$ before filer it, then remove the CH$_2$Cl$_2$ at reduced pressure to obtain the crude product—dimethyl amine intermediate. Dissolve it again with a few amount of CH$_2$Cl$_2$ and add the dilute hydrochloric acid solution (equivalent to dimethyl amine intermediate) with stirring where the pH value of aqueous solution shall be tested during stirring and the dripping of hydrochloric acid solution shall be stopped when it becomes 4-5. Collect the aqueous phase and dry it through freezing to get Compound 22.

Dimethyl amine intermediate: $^1$H NMR (CDCl$_3$, 400 MHz) δ 3.76 (t, J=10.0 Hz, 1H), 2.96 (s, 1H), 2.49-2.67 (m, 3H), 2.28-2.34 (m, 1H), 2.30-2.34 (m, 2H) 2.18 (s, 6H), 2.09 (br s, 2H), 1.96 (d, J=11.2 Hz, 1H) 1.67-1.73 (m, 2H) 1.60 (s, 3H), 1.22 (br s, 3H), 1.18 (br s, 2H); 13C NMR (CDCl3, 300 MHz) δ 177.0, 131.8, 131.3, 84.0, 80.2, 58.3, 58.1, 50.9, 46.0, 44.6,38.4, 353, 30.0, 272, 23.7, 22.8.

Compound 22: $[α]_D^{20}$=−42.0 (c=10, H$_2$O); IR (KBr): 3334, 2927, 2856, 1767, 1467, 992, 967, 874, 831, 719, 669, 626, 504 cm-1; $^1$H NMR (D$_2$O, 400 MHz) δ 4.14 (t, J=10.3 Hz, 1H), 3.51 (q, J=12.6 Hz, 1H), 3.40 (dd, J=13.3, 2.9 Hz, 1H), 3.18-3.04 (m, 1H), 2.96 (d, J=10.6 Hz, 6H), 2.67 (d, J=10.2 Hz, 1H), 2.37 (dd, J=16.2, 8.1 Hz, 1H), 2.27-2.05 (m, 4H), 1.87 (d, J=12.9 Hz, 1H), 1.73 (dd, J=19.5, 11.7 Hz, 2H), 1.66 (s, 3H), 1.46-131 (m, 2H), 1.26 (s, 3H) $^{13}$C NMR (CDCl$_3$, 100 MHz) δ 178.4, 132.6, 131.4, 85.1, 80.7, 56.9, 55.6, 49.9, 45.1, 42.3, 41.5, 39.2, 34.4, 29.5, 25.9, 23.2, 21.4. HRMS calcd for C$_{17}$H$_{27}$NO$_3$ [M$^+$H]$^+$ 294.1991, found 294.2069.

Preparation of Compound 23:

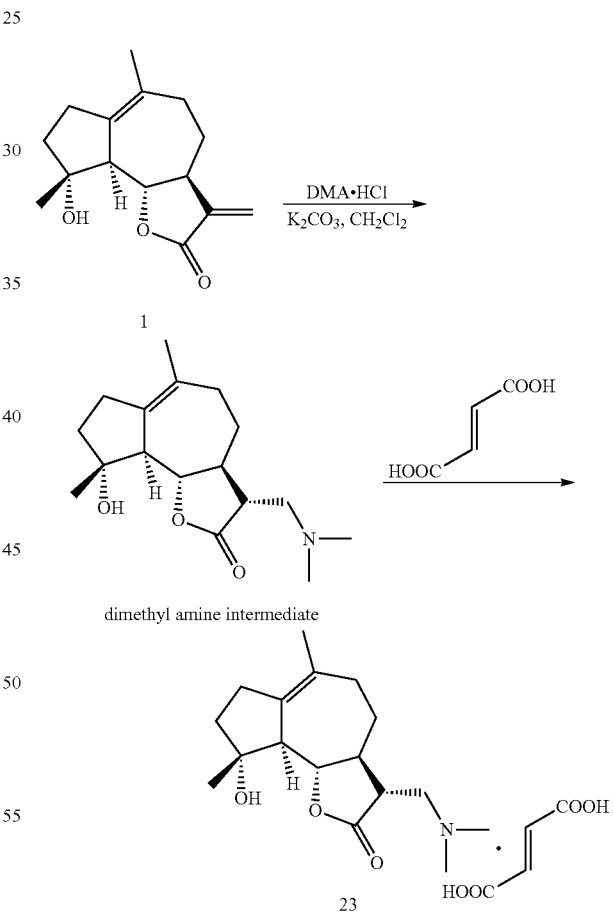

Mix dimethylamine hydrochloride (1.5 g, 18 mmol) and K$_2$CO$_3$ (5.0 g, 36 mmol) and then add them into 10 ml CH$_2$Cl$_2$ to stir 15 minutes, then filler under pressure and directly add into Compound 5 (300 mg, 1.2 mmol) and stir for 3 h at room temperature. Remove the solvent at reduced pressure and dissolve it with a few amount of CH$_2$Cl$_2$, then wash it three times rapidly with water and dry with Na$_2$SO$_4$ before filter it. Remove the CH$_2$Cl$_2$ at reduced pressure to yield the crude product—dimethyl amine intermediate, then dissolve it again with a few amount of CH$_2$Cl$_2$ and add fumaric acid (equivalent to dimethyl amine intermediate) with stirring. Then concentrate and dry it to get Compound 23. $^1$H NMR (DMSO, 400 MHz) δ 6.58 (s, 2H), 3.80 (t, J=10.3 Hz, 1H), 2.64 (s, 3H), 2.49-2.53 (m, 3H), 2.26-2.27 (m, 1H), 2.23 (s, 6H), 1.96-2.10 (m, 6H), 1.60 (s, 3H), 1.57-1.59 (m, 2H), 1.23-1.25 (m, 1H), 1.15 (s, 3H); $^{13}$C NMR (CDCl$_3$, 100 MHz) 177.8, 167.6, 1352, 133.7, 131.4, 83.4, 8031, 58.0, 57.1, 51.7, 45.2, 43.6, 41.0, 353, 302, 27.0, 242, 232.

Preparation of Compound 24:

Dissolve Compound 1 (628 mg, 12.5 mmol) in 35 ml CH$_2$Cl$_2$ and then add m-CPBA (680 mg, 4.0 mmol). Place and stir the reaction system at room temperature and monitor the reaction with TCL. After the raw materials disappear, pour the reaction mixture into 5% NaHCO$_3$ (60 mL) and wash the organic phase with water (20 ml), then collect the organic phase and dry it with Na$_2$SO$_4$ before filer it, then dry it through rotary evaporation to get the crude product, then purify it with silica gel column to get Compound 24. $^1$H NMR (CDCl3, 400 MHz) δ 6.17 (d, J=32 Hz, 1H), 5.47 (d, J=2.8 Hz, 11H), 4.04 (t, J=10.8 Hz, 1H, 2.36-2.20 (m, 4H), 2.03-1.08 (m, 4H), 1.68-1.62 (m, 1H), 1.46 (s, 3H), 1.46 (d, J=12.8 Hz, 1H), 1.29 (s, 3H); $^{13}$C NMR (CDCl3, 100 MHz) δ 169.5, 137.9, 119.5, 81.7, 79.5, 69.7, 62.1, 55.3, 49.2, 37.2, 33.2, 29.3, 23.1, 23.0, 21.8.

Preparation of Compound 25:

According to the paper "Hongquan Yin, Xiulan Qi, Huiming Hua, Yuehu Pei, Study on Chemical Ingredients of Aplotaxis Auriculata, Chin J Med Chem, 2005, Vol 15, No. 4, P217-220", it is produced through separating and purifying from aplotaxis auriculata.

Preparation of Compound 26 and Compound 30:

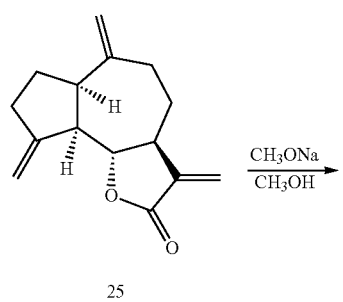

25

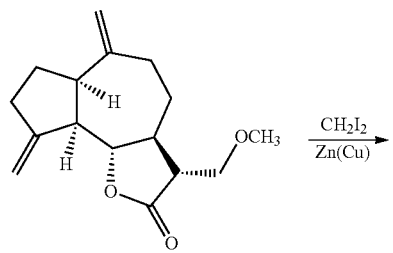

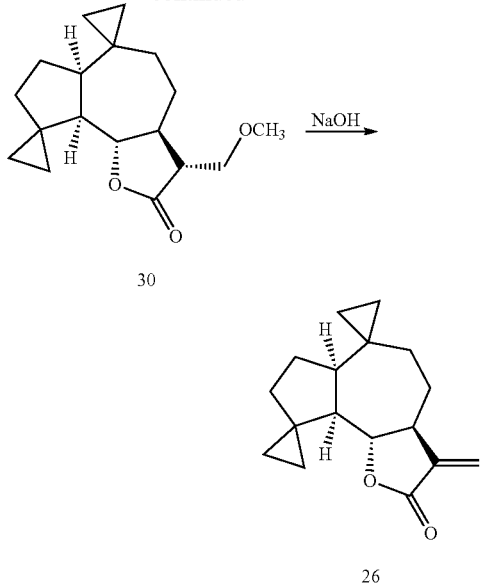

30

26

Stir the methanol solution of Compound 25 (150 mg, 0.65 mmol) and sodium methoxide (20 mg, 0.37 mmol) at 30° C. for 10 hours. After TLC test is finished, pour the reaction solution into ice water, extract it with ethyl acetate four times and mix the layers of ethyl acetate, then wash it with 5% hydrochloric acid, saturated NaHCO$_3$ aqueous solution and saturated saline solution in turn. Dry with anhydrous magnesium sulfate, then filter, concentrate and purify it with silica gel column to get the methoxylation product (136 mg, 80%).

$^1$H-NMR (400 MHz, CDCl$_3$) δ 5.19 (d, J=1.6 Hz, 1H) 5.03 (d, J=1.6 Hz, 1H), 4.87 (s, 1H), 4.76 (s, 1H, 3.93 (t, J=9.2 Hz, 1H), 3.70 (dd, J=4.4, 9.8 Hz, H), 3.63 (dd, J=3.2, 9.8 Hz, 1H), 3.37 (s, 3H), 2.90 (m, 1H), 2.83 (m, 1H), 2.51 (m, 2H), 2.49 (m, 1H), 2.44 (m, 1H), 2.38 (m, 1H), 2.19 (m, 1H), 2.07 (m, 1H), 1.95 (m, 1H), 1.86 (m, 1H), 1.32 (m, 1H); $^{13}$C-NMR (100 MHz, CDCl$_3$) δ 175.7, 151.8, 149.9, 111.5, 108.8, 85.3, 68.9, 59.0, 51.7, 47.7, 46.9, 43.9, 37.7, 32.5, 32.4, 30.1.

Add Zn—Cu alloy (812 mg) and anhydrous ether (4 mL) in a dual-port bottle connected with condenser pipe and dry pipe, then add one granule of iodine and stir it until the color of iodine disappears. Add the ether solution (2 mL) of methoxylation product (262 mg, 1 mmol) and diiodomethane (0.8 mL, 10 mmol) and then reflux it for 72 hours. After TLC shows the reaction is completed, pour out the ether solution and wash the residual solid two times with ether (3 mL), mix the ether layers and wash it respectively with saturated NH$_4$Cl aqueous solution and water (10 mL) then dry it with anhydrous sodium sulfate before filter and concentrate. Purify it with chromatography column to get the product which is white solid Compound 30 (206 mg, 71%). $^1$H-NMR (400 MHz, CDCl$_3$) δ 4.20 (m, 1H), 3.65 (dd, J=3.9, 9.9 Hz, 1H), 3.59 (dd, J=3.0, 9.9 Hz, 1H), 3.34 (s, 1H), 2.30-2.40 (m, 3H), 1.92-2.07 (m, 2H), 1.15-1.70 (m, 7H), 0.85 (m, 1H), 0.70 (m, 1H), 0.50 (m, 1H), 0.40 (m, 1H), 0.16-0.36 (m, 4H); $^{13}$C-NMR (100 MHz, CDCl$_3$) δ 176.4, 83.9, 69.2, 59.2, 51.5, 47.9, 473, 443, 36.2, 35.9, 29.0, 273, 26.7, 18.5, 12.5, 10.4, 10.0, 8.8; ESI-HRMS m/z: 291.1964 [M+H].

Dissolve Compound 30 (0.023 g, 0.080 mmol) in acetonitrile (0.52 mL), then add 4M NaOH aqueous solution (0.11 mL) and reflux 5 hours, after TLC test shows the reaction is completed, cool it to room temperature before add 10% hydrochloric acid to adjust the pH value to 3. Add ethyl acetate (20 mL) and wash twice with water (2×20 mL), then extract the aqueous phase twice with ethyl acetate(2×20 mL), mix the organic layers and dry it with anhydrous sodium sulfate, then filter and concentrate it before separate with chromatography column to get the product which is white solid 26 (0.019 g, 94%).

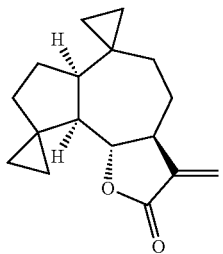

26

Molecular formula: $C_{17}H_{22}O_2$
Molecular weight: 258
Form: white amorphous powder
Spectrum data:
$^1$H-NMR (400 MHz, CDCl$_3$) δ 6.17 (d, J=3.2 Hz, 1H), 5.45 (d, J=3.2 Hz, 1H), 4.24 (dd, J=8.8, 10.8 Hz, 1H), 2.87 (m, 1H), 2.20 (m, 1H), 2.07 (m, 1H), 1.95 (dd, J=8.8, 10.4 Hz, 1H), 1.71 (m, 2H), 1.37-1.61 (m, 5H), 0.98 (m, 1H), 0.64 (m, 1H), 0.49 (m, 1H), 0.43 (m, 1H), 0.27-0.37 (m, 4H); $^{13}$C NMR (100 MHz, CDCl$_3$) δ 169.4, 139.4, 118.5, 82.5, 51.6, 47.4, 442, 34.2, 32.8, 26.4, 26.2, 25.3, 17.4, 11.1, 10.7, 10.5, 7.8; ESI-HRMS m/z: 259.1692 [M+H].

Preparation of Compound 27:

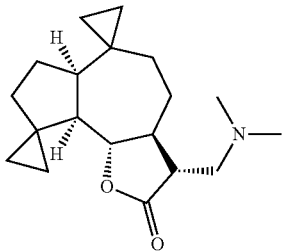

27

Suspend dimethylamine hydrochloride (245 mg) in 11 mL CH$_2$Cl$_2$ solution, then add K$_2$CO$_3$ (380 mg) and stir 0.5 hour, then add Compound 26 (42 mg) and reflux 4 hours, then separate with silica gel column (petroleum ether ethyl acetate:=70:30) to get the oily Compound 27 with the yield: 78%

Molecular formula: $C_{19}H_{29}NO_2$
Molecular weight: 303
Form: oily liquid
Spectrum data:
$^1$H-NMR (400 MHz, CDCl$_3$) δ4.19 (dd, J=9.5, 102 Hz, 1H), 2.66 (dd, J=12.8, 4.8 Hz, 1H), 2.49 (dd, J=12.8, 6.8 Hz, 1H), 2.25-2.38 (m, 2H), 2.21 (s, 6H), 1.98-2.12 (m, 2H), 1.80-1.84 (m, 1H), 1.68 (m, 1H), 1.27-1.48 (m, 5H), 1.11 (m, 1H), 1.01 (m, 1H), 0.69 (m, 1H), 0.46 (m, 1H), 0.18-137 (m, 4H), 0.11 (m, 2H); $^{13}$C NMR (100 MHz, CDCl$_3$) δ 181.3, 82.8, 58.0, 50.8, 46.4, 46.0, 45.0, 44.6, 35.2, 34.9, 28.2, 26.3, 25.7, 17.5, 11.5, 9.6, 92, 7.9; ESI-HRMS m/z: 304.2273 [M+H].

Synthesis Method of Compound 28:

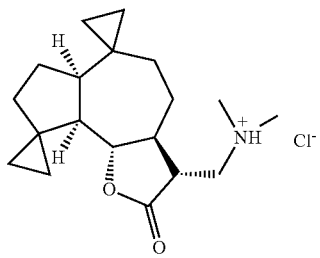

28

Dissolve Compound 27 (38 mg) in 2 mL CH$_2$Cl$_2$. Slowly add 0.05 M dilute hydrochloric acid with stirring until the pH value becomes 4. Separate the aqueous phase, wash once with CH2Cl2. Freeze, and dry the aqueous phase to get Compound 28 (31 mg) with a yield of 73%.

Molecular formula: $C_{19}H_{30}NO_2Cl$
Molecular weight: 339
Form: White solid
Spectrum data:
$^1$H-NMR (400 MHz, D$_2$O) δ 4.42 (m, 1H), 331-337 (m, 1H), 3.21-3.25 (n, 1H), 2.92 (m, 1H), 2.82 (s, 3H), 2.80 (s, 3H), 2.11-2.26 (m, 2H), 1.94 (m, 1H), 1.79 (m, 11H), 1.39-1.58 (m, 5H), 1.23 (m, 1H), 1.13 (m, 1H), 0.69 (m, 1H), 0.46 (m, 1H, 0.18-1.33 (m, 4H), 0.11 (m, 2H); $^{13}$C NMR (100 MHz, D$_2$O) 178.2, 85.8, 56.0, 51.0, 47.2, 45.9, 44.8, 42.5, 42.2, 35.7, 35.2, 27.5, 272, 26.6, 183, 12.2, 103, 9.8, 8.6; ESI-HRMS m/z: 304.2271 [M+H].

Synthesis of Compound 29:

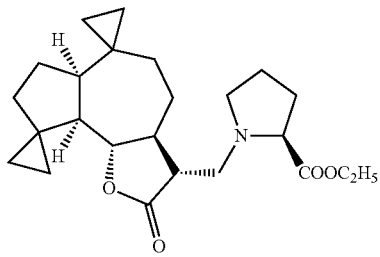

(29)

Add 20 mg Compound 26 into the reaction flask and dissolve it with 1 mL THF, then add 86 mg proline ethyl ester hydrochloride and 0.2 mL DBU, stir for 24 hours before purify it with chromatography column to get Compound 29 (12 mg) with a yield: 39%.

Molecular formula: $C_{24}H_{35}NO_4$
Molecular weight: 401
Form: colorless oily compound
Spectrum data:
$^1$H NMR (400 MHz, CDCl$_3$): δ 4.10-4.22 (m, 3H) 3.31 (dd, J=8.8, 5.2 Hz, 1H), 3.05 (dd, J=13.2, 5.2 Hz, 1H), 2.91-2.96 (m, 1H), 2.86 (dd, J=132, 3.6 Hz, 1H), 2.37-2.49 (m, 3H) 2.23-2.29 (m, 1H) 1.96-2.11 (m, 3H), 1.73-1.94 (m, 3H), 1.57-1.69 (m, 3H), 1.40 -1.47 (m, 1H), 1.17-136 (m, 6H), 0.83-0.89 (m, 1H), 0.70-0.75 (m, 1H), 0.48-0.53 (m, 1H), 0.40-0.45 (m, 1H), 0.26-036 (m, 2H), 0.17-0.24 (m, 2H); $^{13}$C NMR (100 MHz, CDCl$_3$): δ 178.3, 174.4, 843, 66.6, 60.6, 53.9, 51.9, 51.7, 47.5, 472, 44.7, 36.6, 362, 293, 29.1, 27.6, 27.0, 24.0, 18.8, 14.5, 12.8, 10.6, 10.1, 9.1; ESI-HRMS m/z: 402.2644 [M+H].

Synthesis Method of Compound (31):

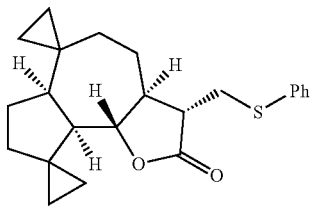

Weigh Compound 26 (51.6 mg) and dissolve DMAP (4 mg) in 2 mL $CH_2Cl_2$, then add 66 mg thiophenol and stir 12 hours, dry it through rotary evaporation and purify it with silica column chromatography to get Compound 31(68 mg).

$^1$H NMR (400 MHz, $CDCl_3$) δ 7.44-7.34 (m, 2H), 7.30 (dd, J=10.3, 4.8 Hz, 2H), 7.20 (t, J=7.3 Hz, 1H), 4.24-4.14 (m, 1H), 3.47 (dd, J=13.8, 4.0 Hz, 1H), 3.11 (dd, J=13.8, 7.0 Hz, 1H), 2.52 (ddd, J=11.2, 7.0, 4.1 Hz, 1H), 2.30 (ddd, J=20.7, 10.6, 4.2 Hz, 1H), 2.21 (dd, J=18.2, 8.9 Hz, 1H), 2.13-2.03 (m, 1H), 1.96-1.86 (m, 1H), 1.73-1.63 (m, 1H), 1.61-1.47 (m, 2H), 1.43 (ddd, J=12.3, 8.5, 3.5 Hz, 1H), 1.39-1.25 (m, 3H), 0.89 (dt, J=9.8, 4.8 Hz, 1H), 0.65 (ddd, J=9.2, 5.4, 3.8 Hz, 1H), 0.42 (tt, J=13.4, 4.6 Hz, 2H), 0.36-0.30 (m, 1H), 0.29-0.21 (m, 2H), 0.18-0.08 (m, 1H); $^{13}$C NMR (100 MHz, $CDCl_3$) δ 177.1, 136.3, 130.0, 129.6, 127.0, 84.2, 77.92, 52.6, 48.3, 47.4, 47.1, 35.9, 35.4, 33.8, 29.7, 27.7, 27.0, 18.8, 12.8, 11.4, 9.3.

Synthesis Method of Compound (32):

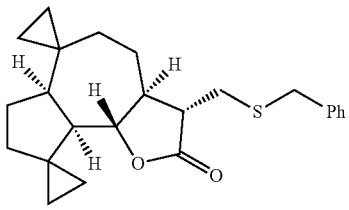

Dissolve Compound 26 (51.6 mg) and 1,8-Diazabicyclo (5.4.0)undec-7-ene (15.2 mg) in 0.5 mL acetonitrile, then add 37.3 mg benzyl mercaptane and stir 24 hours, then dry through rotary evaporation, then purify it with silica column chromatography to get Compound 32 (75 mg). $^1$H NMR (400 MHz, $CDCl_3$) δ 7.30-7.23 (m, 4H), 7.22-7.17 (m, 1H), 4.13 (t, J=9.9 Hz, 1H), 3.77-3.63 (m, 2H), 2.80-2.66 (m, 2H), 2.35 (dt, J=10.5, 5.1 Hz, 1H), 2.28-2.14 (m, 2H), 1.89 (ddd, J=14.0, 10.1, 5.2 Hz, 2H), 1.67-1.49 (m, 2H), 1.48-1.38 (m, 2H), 1.38-1.30 (m, 1H), 1.30-1.17 (m, 2H), 0.83 (dt, J=9.7, 4.9 Hz, 1H), 0.63 (ddd, J=9.4, 5.4, 4.0 Hz, 1H), 0.48-0.40 (m, 1H), 0.36 (dt, J=8.9, 4.5 Hz, 1H), 0.33-0.25 (m, 1H), 0.24-0.13 (m, 3H); $^{13}$C NMR (100 MHz, $CDCl_3$) δ 177.4, 138.6, 129.5, 129.0, 127.6, 84.3, 52.2, 48.0, 47.7, 46.8, 38.1, 36.1, 36.0, 30.7, 29.6, 27.8, 27.1, 18.9, 13.0, 11.2, 11.0, 9.3.

Synthesis Method of Compound (33):

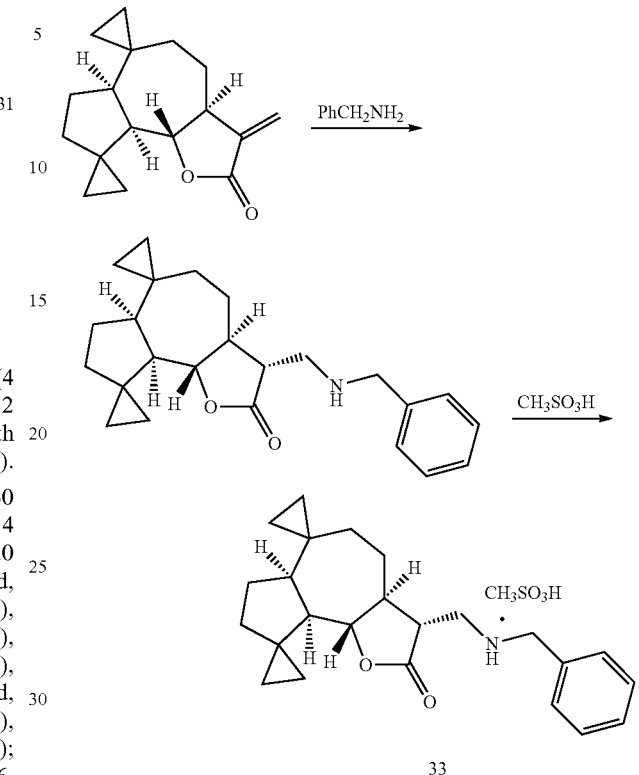

Dissolve Compound 26 (51.6 mg) in 1 mL methanol, then add 321 mg benzylamine and stir 24 hours, then dry it through rotary evaporation, then purify it with silica column chromatography to get the intermediate (76 mg). Dissolve it in 5 mL methanol and add 21 mg methane sulfonic acid, then stir it 10 minutes and dry with dry evaporation to get Compound 33 (97 mg).

$^1$H NMR (400 MHz, MeOD) δ 7.47 (d, J=38.9 Hz, 5H), 4.41 (t, J=9.9 Hz, 1H), 4.27 (q, J=13.1 Hz, 2H), 3.26 (s, 1H), 2.93-2.79 (m, 1H), 2.67 (s, 3H), 2.39-2.28 (m, 1H), 2.17 (t, J=16.3 Hz, 1H), 2.04 (t, J=9.7 Hz, 1H), 1.86 (d, J=8.2 Hz, 1H), 1.60 (dd, J=17.1, 7.0 Hz, 2H), 1.45 (d, J=35.5 Hz, 3H), 1.30 (dt, J=28.7, 13.8 Hz, 3H), 0.83 (d, J=4.0 Hz, 1H), 0.62 (s, 1H), 0.48 (d, J=3.8 Hz, 1H), 0.41 (d, J=3.9 Hz, 1H), 0.30 (d, J=4.0 Hz, 2H), 0.21 (s, 2H); $^{13}$C NMR (100 MHz, MeOD) δ 178.38, 132.13, 131.14, 130.72, 130.28, 86.43, 52.59, 52.52, 48.62, 46.81, 46.39, 44.39, 39.60, 36.78, 36.68, 29.12, 28.21, 27.69, 19.31, 13.06, 11.09, 10.81, 9.44.

Synthesis Method of Compound (34):

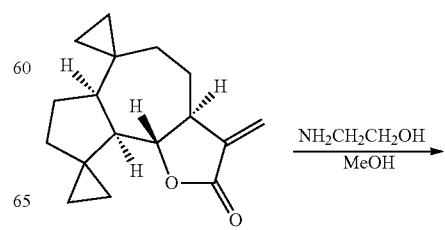

21
-continued

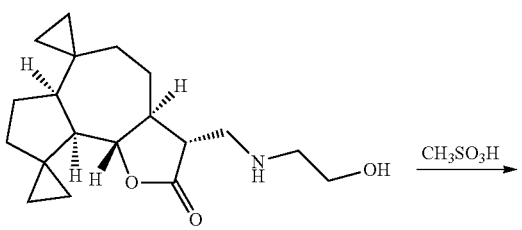

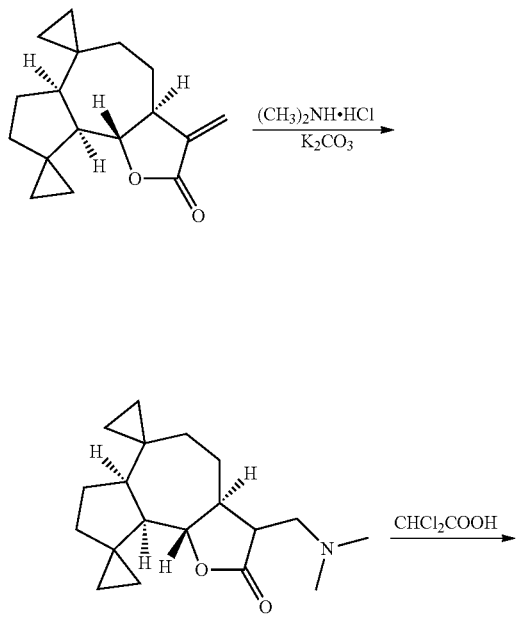

34

Dissolve Compound 26 (103 mg) in 2 mL methanol, add 366 mg aminoethanol and stir 24 hours, then purify it with silica column chromatography to get 118 g amine addition intermediate, then dissolve it in 5 mL methanol and add 35.6 mg methane sulfonic acid, then stir it 10 minutes and dry with dry evaporation to get Compound 34 (153 mg).

$^1$H NMR (400 MHz, D$_2$O) δ 4.60 (t, J=10.1 Hz, 1H), 3.85 (t, J=5.0 Hz, 2H), 3.41-3.31 (m, 2H), 3.29-3.18 (m, 2H), 2.97-2.84 (m, 1H), 2.78 (s, 3H), 2.33 (q, J=8.8 Hz, 2H), 2.03 (t, J=9.8 Hz, 1H), 1.96-1.86 (m, 1H), 1.67 (dd, J=11.8, 7.7 Hz, 1H), 1.59-1.37 (m, 5H), 1.35-1.23 (m, 1H), 0.83-0.74 (m, 1H), 0.55-0.38 (m, 3H), 0.38-0.25 (m, 3H), 0.24-0.19 (m, 1H):

$^{13}$C NMR (100 MHz, D$_2$O) δ 178.39, 85.67, 56.28, 50.62, 49.68, 46.96, 45.74, 45.67, 43.11, 38.58, 35.95, 35.62, 27.66, 27.22, 26.69, 18.27, 12.28, 10.14, 9.49, 8.72.

Synthesis Method of Compound (35):

22
-continued

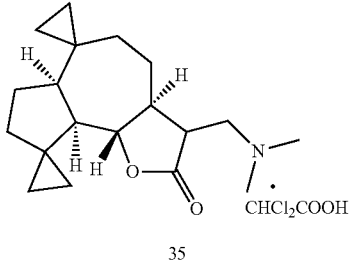

35

Weigh Compound 26 (103 mg) and dimethylamine hydrochloride (489 mg) to dissolve in 20 mL CH$_2$Cl$_2$, add 1.66 g K$_2$CO$_3$ and reflux 6 hours, filter it before drying it through rotary evaporation, and then purify it with silica column chromatography to get Compound 27 (110 mg). Weigh 49 mg Compound 27 to dissolve in 1 mL methanol and add 20.9 mg dichloroacetic acid before stir 10 minutes, and then dry it through rotary evaporation to get Compound 35 (69 mg).

$^1$H NMR (400 MHz, MeOD) δ 5.91 (s, 1H), 4.41 (t, J=10.1 Hz, 1H), 3.37 (dd, J=13.3, 9.2 Hz, 1H), 3.22 (dd, J=13.3, 4.0 Hz, 1H), 2.98-2.91 (m, 1H), 2.85 (s, 6H), 2.35 (dd, J=17.4, 9.1 Hz, 1H), 2.25-2.14 (m, 1H), 2.08-2.00 (m, 1H), 1.98-1.88 (m, 1H), 1.69-1.56 (m, 2H), 1.56-1.44 (m, 3H), 1.40-1.22 (m, 2H), 0.85 (dt, J=9.6, 4.8 Hz, 1H), 0.63 (ddd, J=9.3, 5.4, 3.9 Hz, 1H), 0.52-0.46 (m, 1H), 0.45-0.39 (m, 1H), 0.35-0.29 (m, 2H), 0.21 (td, J=9.5, 5.2 Hz, 2H); $^{13}$C NMR (100 MHz, MeOD) δ 178.45, 170.46, 86.32, 70.47, 57.60, 52.72, 48.77, 47.52, 44.52, 43.69, 36.93, 36.85, 29.11, 28.36, 27.85, 19.45, 13.22, 11.23, 10.93, 9.58.

Synthesis Method of Compound (36):

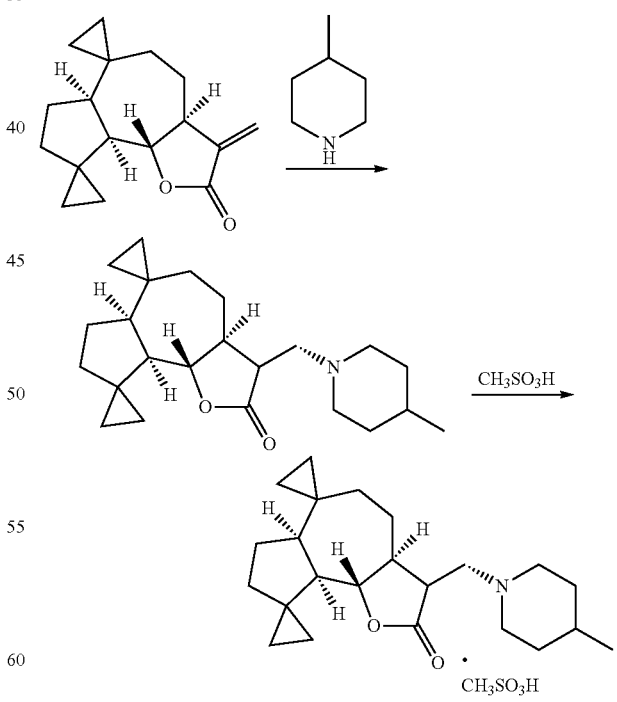

36

Weigh Compound 26 (50.0 mg) to dissolve it in 1 mL anhydrous methanol, add 0.27 mL piperidine and allow them to react overnight, then concentrate it before purify it with silica column chromatography to get 50 mg amine addition intermediate compound, then dissolve it in 10 mL methanol and add methane sulfonic acid in equivalent amount, then dry it through rotary evaporation to get Compound 36 (63 mg). $^1$H NMR (CD$_3$OD, 400 MHz) δ 0.13-0.18 (m, 2H), 0.24-0.30 (m, 2H), 0.33-0.38 (m, 1H), 0.41-0.45 (m, 1H), 0.55-0.59 (m, 1H), 0.76-0.81 (m, 1H), 0.92 (d, J=6.5 Hz, 3H), 1.19-1.66 (m, 9H), 1.81-1.92 (m, 3H), 1.96-2.01 (m, 1H), 2.12-2.18 (m, 1H), 2.26-2.31 (m, 1H), 2.61 (s, 3H), 2.92-3.02 (m, 3H), 3.18-3.36 (m, 3H), 3.53 (t, J=13.6 Hz, 2H), 4.37 (t, J=10.1 Hz, 1H); $^{13}$C NMR (CD$_3$OD, 100 MHz) δ 9.4, 10.8, 11.1, 13.1, 19.3, 21.4, 27.7, 28.2, 28.9, 29.5, 32.4, 32.4, 36.7, 36.8, 39.7, 43.1, 47.7, 52.4, 54.2, 55.4, 56.6, 86.0, 178.

Synthesis Method of Compound (37):

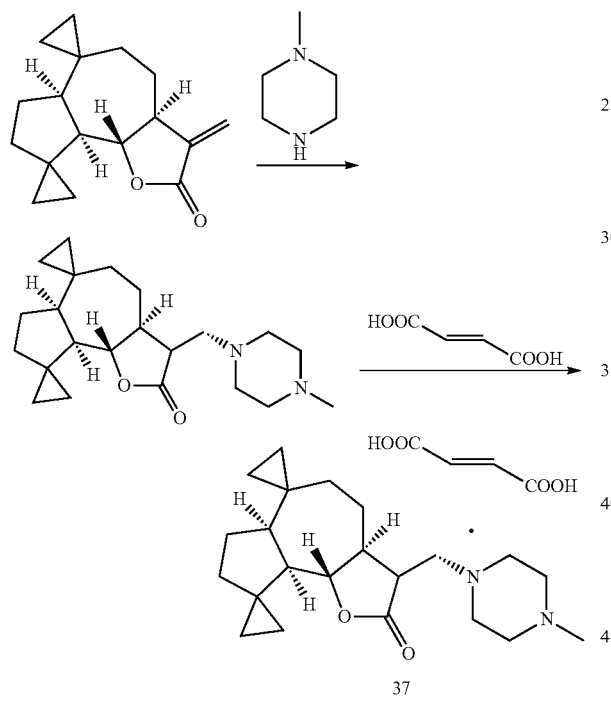

Weigh Compound 26 (50.0 mg) to dissolve it in 1 mL anhydrous methanol, add 0.30 mL piperazine and allow them to react overnight, then concentrate it before purify it with silica column chromatography to get 51 mg amine addition intermediate compound, then dissolve it in 10 mL methanol and add fumaric acid in equivalent amount, then dry it through rotary evaporation to get Compound 37 (62 mg).

$^1$H NMR (CD$_3$OD, 400 MHz) δ 0.07-0.13 (m, 2H), 0.17-0.22 (m, 2H), 0.28-0.32 (m, 1H), 0.36-0.40 (m, 1H), 0.49-0.53 (m, 1H), 0.72-0.76 (m, 1H), 1.09-1.58 (m, 7H), 1.84-1.95 (m, 2H), 2.06-2.12 (m, 1H), 2.18-2.25 (m, 1H), 2.37-2.43 (m, 1H), 2.52-2.69 (m, 6H), 2.69 (s, 3H), 3.10 (brs, 3H), 3.16-3.17 (m, 1H), 4.19 (t, J=10.0 Hz, 1H), 6.56 (s, 2H) $^{13}$C NMR (CD$_3$OD, 100 MHz) δ 9.5, 11.1, 11.2, 13.0, 19.4, 27.7, 28.3, 29.7, 36.8, 36.8, 43.4, 46.4, 47.9, 48.9, 51.6, 53.1, 54.5, 57.2, 85.6, 136, 170.6, 179.9.

Synthesis Method of Compound (38):

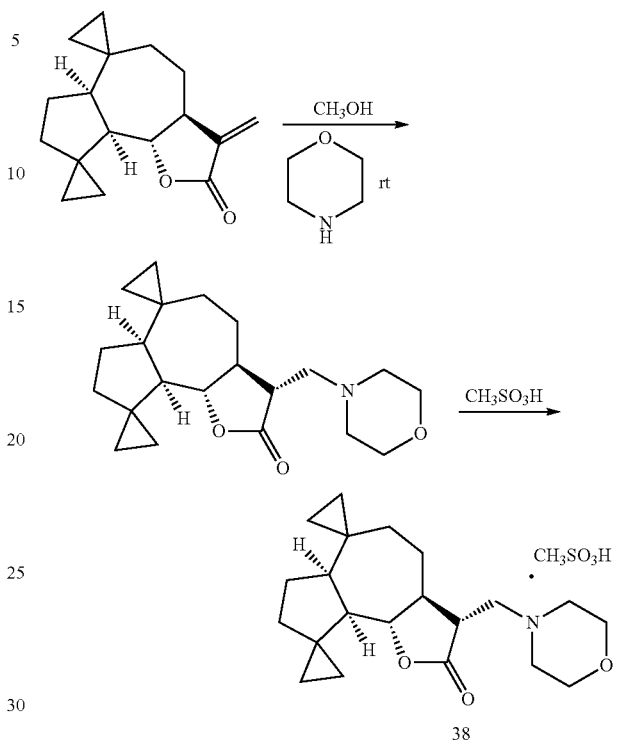

Dissolve Compound 26 (100 mg, 0.39 mmol) in anhydrous methanol (20 mL), then add morpholine (508 mg, 5.85 mmol) and stir overnight at room temperature. Separate and purify it through silica column chromatography to get the product (100 mg, 0.29 mmol), then dissolve the product in anhydrous methanol (5 mL), add methanesulfonic acid (27.8 mg, 0.29 mmol), then dry the methanol through rotary evaporation to get Compound 38 (127.8 mg).

$^1$H NMR (400 MHz, D$_2$O) δ 4.56 (t, J=10.1 Hz, 1H), 4.10 (s, 2H), 3.92 (m, J=17.5, 12.5 Hz, 2H), 3.67-3.46 (m, 3H), 3.39 (dd, J=13.8, 3.3 Hz, 1H), 3.35-3.25 (m, 2H), 3.12-3.01 (m, 1H), 2.77 (s, 3H), 2.34 (dt, J=15.8, 7.9 Hz, 2H), 2.05 (t, J=9.9 Hz, 1H), 1.93 (s, 1H), 1.76-1.44 (m, 5H), 1.43-1.33 (m, 1H), 1.34-1.22 (m, 1H), 0.88-0.74 (m, 1H), 0.65-0.52 (m, 1H), 0.52-0.18 (m, 6H); $^{13}$C NMR (100 MHz, D$_2$O) 178.38, 85.98, 63.53, 55.30, 50.93, 48.80, 47.00, 45.84, 41.70, 38.45, 35.16, 34.68, 27.34, 26.77, 26.31, 17.94, 11.76, 9.99, 9.71, 8.11.

Synthesis Method of Compound (39):

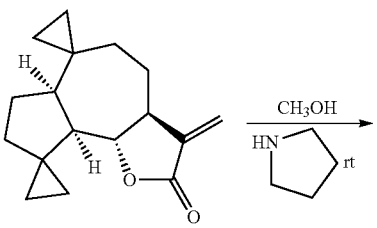

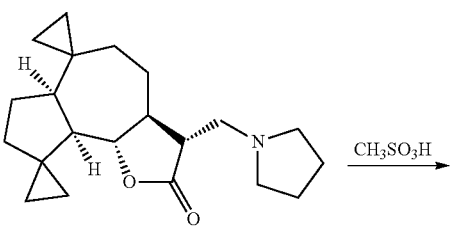

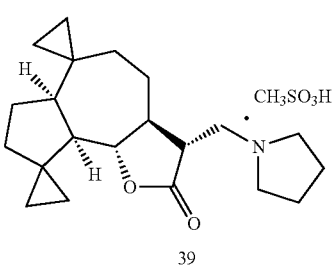
39

Dissolve Compound 26 (50 mg, 0.195 mmol) in anhydrous methanol (5 mL), then add pyrrolidine (208 mg, 2.93 mmol) and stir overnight at room temperature. Separate and purify it through silica column chromatography to get the product (52 mg, 0.16 mmol), dissolve the product in anhydrous methanol (5 mL), add methanesulfonic acid (15.2 mg, 0.16 mmol), then dry the methanol through rotary evaporation to get Compound 39 (57.2 mg).

$^1$H NMR (400 MHz, D$_2$O) δ 4.44 (t, J=10.0 Hz, 1H), 3.79-3.58 (m, 2H), 3.50 (dd, J=13.4, 9.5 Hz, 1H), 3.35 (dd, J=13.5, 3.6 Hz, 1H), 3.21-3.03 (m, 2H), 2.90 (dd, J=5.9, 3.2 Hz, 1H), 2.73 (s, 3H), 2.33 (d, J=8.5 Hz, 1H), 2.24-2.08 (m, 3H), 2.06-1.95 (m, 3H), 1.92 (s, 1H), 1.52 (dt, J=24.8, 8.8 Hz, 5H), 1.33-1.15 (m, 2H), 0.87-0.71 (m, 1H), 0.65-0.53 (m, 1H), 0.46-0.08 (m, 6H); $^{13}$C NMR (100 MHz, D$_2$O) δ 178.08, 85.50, 55.92, 54.06, 52.97, 50.74, 46.95, 45.81, 43.22, 38.44, 35.58, 35.18, 27.47, 26.99, 26.50, 22.66, 22.54, 18.10, 12.03, 10.04, 9.54, 8.43.

Synthesis Method of Compound (40):

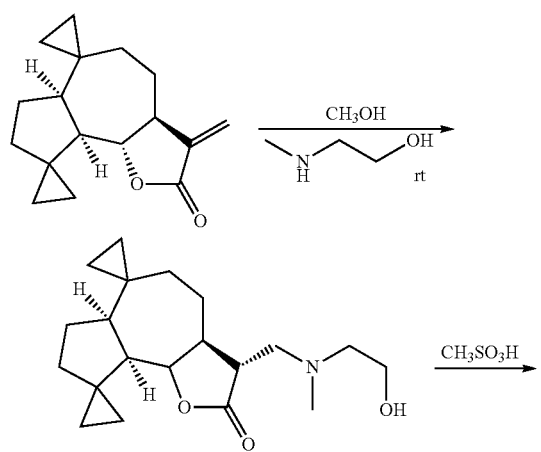

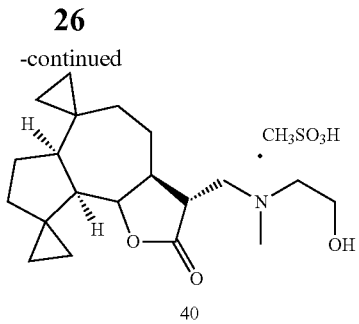
40

Compound 26 (100 mg, 0.39 mmol) in anhydrous methanol (2 mL), then add N-methylethanolamine (438 mg, 5.85 mmol) and stir overnight at room temperature. Separate and purify through silica column chromatography to get the product (100 mg, 0.30 mmol), dissolve the product in CH$_2$Cl$_2$ (5 mL), add methanesulfonic acid (28.8 mg, 0.30 mmol), then dry the CH$_2$Cl$_2$ through rotary evaporation to get Compound 40 (128.8 mg).

$^1$H NMR (400 MHz, CDCl$_3$) δ 4.36 (t, J=9.9 Hz, 1H), 3.92 (s, 2H), 3.65-3.43 (m, 2H), 3.34 (s, 2H), 3.01 (s, 3H), 2.98-2.83 (m, 1H), 2.71 (s, J=2.8 Hz, 3H), 2.37-2.22 (m, 1H), 2.19-2.10 (m, 2H), 2.05-1.88 (m, 2H), 1.57 (m, J=29.9, 18.2 Hz, 5H), 1.31 (d, J=10.9 Hz, 1H), 1.21 (s, 1H), 0.78 (m, 1H), 0.59 (m, 1H), 0.54-0.06 (m, 6H).

Synthesis Method of Compound (41):

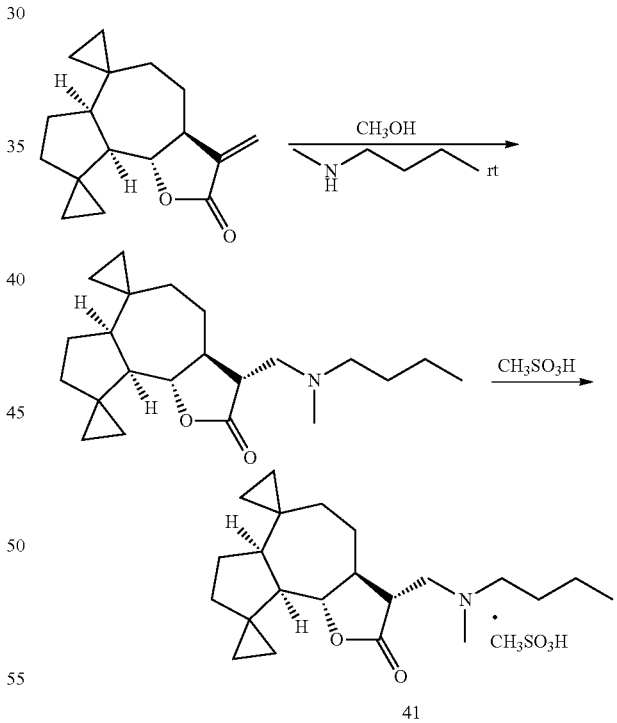
41

Dissolve Compound 26 (50-mg, 0.195 mmol) in anhydrous methanol (2 mL), then add N-Methylbutylamine (254 mg, 2.93 mmol) and stir overnight at room temperature. Separate and purify it through silica column chromatography to get the amine addition intermediate product (50 mg, 0.14 mmol), dissolve the product in CH$_2$Cl$_2$ (5 mL), add methanesulfonic acid (13.9 mg, 0.14 mmol), then dry the CH$_2$Cl$_2$ through rotary evaporation to get Compound 41 (63.9 mg).

$^1$H NMR (400 MHz, D$_2$O) δ 4.60 (s, 1H), 3.59-3.07 (m, 4H), 3.06-2.96 (m, 1H), 2.90 (s, 3H), 2.77 (s, 3H), 2.32 (dd, J=18.0, 8.9 Hz, 2H), 2.07-1.97 (m, 1H), 1.94-1.81 (m, 1H), 1.76-1.62 (m, 3H), 1.61-1.51 (m, 2H), 1.48 (d, J=8.1 Hz, 1H), 1.45-1.24 (m, 5H), 0.91 (t, J=7.4 Hz, 3H), 0.83-0.76 (m, 1H), 0.57-0.49 (m, 1H), 0.45 (ddd, J=17.8, 8.7, 4.7 Hz, 2H), 0.38-0.24 (m, 3H), 0.23-0.17 (m, 1H).

Synthesis Method of Compound 42-45:

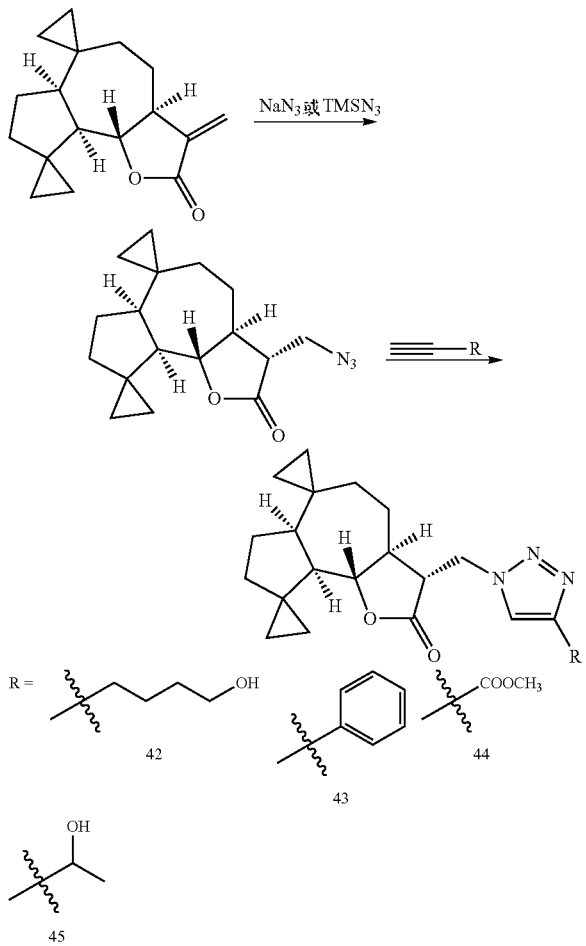

Add trimethylsilyl azide (575 mg, 5.0 mmol) and acetic acid (300 mg, 5.0 mmol) in 50 mL round bottom flask, agitate 20 minutes at room temperature and then add Compound 26 (258 mg, 1.0 mmol) and catalytic amount of thiethylamine (20.2 mg, 0.2 mmol) in the reaction solution, heat it to 60° C. and stir it until the reaction is completed (TLC test). Pour the reaction mixture into appropriate amount ice water and extract it with ethyl acetate (50 mL×3), then wash separately with saturated NaHCO$_3$ solution (20 mL×3) and saturated saline solution (20 mL×3) in turn, then dry it with anhydrous sodium sulfate. Filter it by suction before concentrate it to get the azidation intermediate.

Take the azidation intermediate (0.25 mmol), sodium ascorbate (10 mg, 0.05 mmol) and copper sulfate pentahydrate (12 mg, 0.05 mmol) into a reaction flask dried in advance, then vacuumize it and charge nitrogen gas before seal the mouth. Then add 5 mL solvent mixture (tert-butyl alcohol: water=1:1) and 5-hexynyl-1-ol (49 mg, 0.5 mmol) and stir it at room temperature until the raw materials are reacted completely (TCL test). Pour the reaction mixture into appropriate amount of ice water and then extract with ethyl acetate (10 mL×3), then wash it with saturated saline solution three times, then dry it with anhydrous sodium sulfate, concentrate it at reduced pressure before purify it through silica gel column chromatography to get Compound 42 (71 mg).

$^1$H NMR (400 MHz, CDCl$_3$) δ 7.40 (s, 1H), 4.73-4.58 (m, 2H), 4.23 (t, J=10.0 Hz, 1H), 3.65 (t, J=6.3 Hz, 2H), 2.73 (t, J=7.4 Hz, 2H), 2.63 (dt, J=11.7, 4.2 Hz, 1H), 2.21 (dd, J=18.0, 9.0 Hz, 1H), 1.96-1.89 (m, 1H), 1.88-1.80 (m, 2H), 1.79-1.69 (m, 3H), 1.59 (dt, J=16.7, 7.6 Hz, 4H), 1.52-1.44 (m, 2H), 1.38-1.29 (m, 2H), 1.27-1.19 (m, 1H), 0.81 (dd, J=9.2, 4.8 Hz, 1H), 0.65-0.54 (m, 1H), 0.47-0.40 (m, 1H), 0.40-0.35 (m, 1H), 0.34-0.27 (m, 1H), 0.23 (m, 3H) $^{13}$C NMR (CDCl$_3$, 100 MHz) 176.1, 149.0, 122.3, 84.9, 62.4, 52.0, 48.6, 47.9, 47.5, 44.6, 36.0, 35.5, 32.4, 28.6, 27.6, 27.0, 25.9, 25.6, 18.6, 12.8, 11.1, 10.9, 9.1.

Employ the above-mentioned method to prepare Compound 43 (70 mg).

$^1$H NMR (400 MHz, CDCl$_3$) δ 7.90 (s, 1H), 7.81 (d, J=7.6 Hz, 2H), 7.39 (t, J=7.4 Hz, 2H), 7.29 (dd, J=14.9, 7.7 Hz, 1H), 4.79-4.65 (m, 2H), 4.20 (t, J=9.9 Hz, 1H), 2.68 (dt, J=8.7, 4.1 Hz, 1H), 2.17 (dd, J=17.9, 8.9 Hz, 1H), 2.07-1.92 (m, 1H), 1.84 (d, J=6.1 Hz, 1H), 1.74 (t, J=9.8 Hz, 1H), 1.63-1.49 (m, 2H), 1.42 (dd, J=13.1, 7.5 Hz, 2H), 1.30 (dt, J=20.0, 9.9 Hz, 2H), 1.24-1.15 (m, 1H), 0.79 (dd, J=17.1, 12.5 Hz, 1H), 0.61-0.51 (m, 1H), 0.37 (dd, J=20.4, 4.1 Hz, 2H), 0.29-0.13 (m, 4H); $^{13}$C NMR (100 MHz, CDCl$_3$) δ 175.54, 148.13, 130.37, 128.88, 128.29, 125.73, 120.84, 84.53, 51.46, 48.24, 47.47, 47.20, 44.21, 35.62, 35.21, 28.27, 27.24, 26.61, 18.29, 12.51, 10.69, 10.42, 8.70.

Employ the above-mentioned method to prepare Compound 44 (63 mg).

$^1$H NMR (400 MHz, CDCl$_3$) δ 8.21 (s, 1H), 4.81-4.68 (m, 2H), 4.28 (dd, J=19.8, 9.6 Hz, 1H), 3.95 (s, 3H), 2.76-2.65 (m, 1H), 2.20 (q, J=9.1 Hz, 1H), 2.04-1.85 (m, 2H), 1.74 (t, J=9.9 Hz, 1H), 1.65 (dd, J=19.0, 10.4 Hz, 1H), 1.60-1.43 (m, 3H), 1.42-1.32 (m, 2H), 1.32-1.19 (m, 1H), 0.81 (dt, J=9.5, 4.7 Hz, 1H), 0.59 (dt, J=9.2, 4.5 Hz, 1H), 0.49-0.36 (m, 2H), 0.36-0.29 (m, 1H), 0.30-0.20 (m, 3H); $^{13}$C NMR (100 MHz, CDCl$_3$) δ 175.09, 160.87, 140.15, 128.87, 84.49, 52.19, 51.58, 48.00, 47.55, 47.51, 44.20, 35.51, 34.96, 28.18, 27.18, 26.54, 18.23, 12.42, 10.76, 10.53, 8.64.

Employ the above-mentioned method to prepare Compound 45 (65 mg).

$^1$H NMR (400 MHz, CDCl$_3$) δ 7.58 (d, J=33.3 Hz, 1H), 5.07 (d, J=4.9 Hz, 1H), 4.78-4.60 (m, 2H), 4.26 (t, J=10.0 Hz, 1H), 2.68 (dt, J=9.5, 4.4 Hz, 1H), 2.23 (dd, J=17.7, 8.7 Hz, 1H), 2.03-1.92 (m, 1H), 1.89-1.73 (m, 2H), 1.69-1.62 (m, 1H), 1.62-1.54 (m, 4H), 1.47 (t, J=12.5 Hz, 2H), 1.35 (dd, J=20.3, 10.3 Hz, 2H), 1.30-1.18 (m, 2H), 0.87-0.77 (m, 1H), 0.67-0.57 (m, 1H), 0.49-0.36 (m, 2H), 0.36-0.29 (m, 1H), 0.25 (m, 3H).

Synthesis Method of Compound (46):

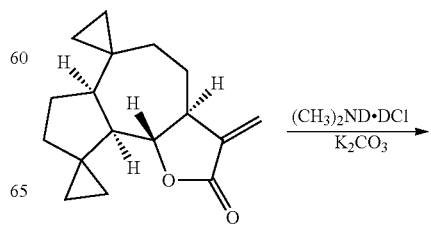

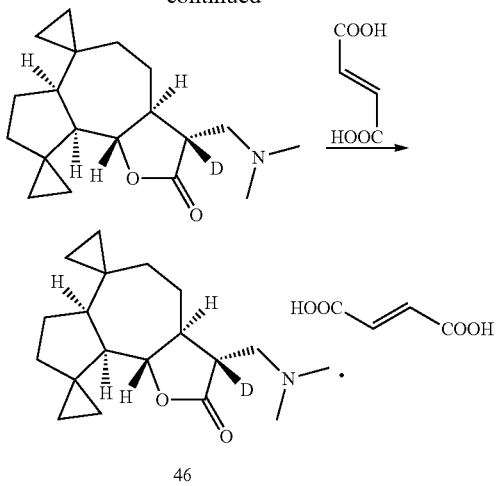

46

Take Compound 26 (167 mg) and deuterated dimethylamine hydrochloride (530 mg) to dissolve in 15 mL CH$_2$Cl$_2$, then add 1.8 g K$_2$CO$_3$ and reflux 24 hours, then filter it before dry it through rotary evaporation, then purify it with silica column chromatography to get the dimethylamino intermediate (150 mg), weigh 49 mg intermediate to dissolve it in 10 mL methanol and then add 18.7 mg fumaric acid to stir 10 minutes, then dry it through rotary evaporation to get Compound 46 (67 mg).

$^1$H NMR (400 MHz, MeOD) δ 6.70 (s, 2H), 4.46 (dd, J=18.9, 8.7 Hz, 1H), 3.46 (dd, J=13.4, 6.3 Hz, 1H), 3.35-3.28 (m, 1H), 2.95 (d, J=14.0 Hz, 6H), 2.38 (dd, J=17.4, 9.1 Hz, 1H), 2.27-2.19 (m, 1H), 2.11-2.03 (m, 1H), 2.01-1.92 (m, 1H), 1.67 (ddd, J=18.7, 11.2, 5.0 Hz, 2H), 1.60-1.48 (m, 3H), 1.45-1.27 (m, 2H), 0.88 (dt, J=9.6, 4.8 Hz, 1H), 0.66 (ddd, J=9.3, 5.4, 3.8 Hz, 1H), 0.56-0.50 (m, 1H), 0.45 (dt, J=9.3, 4.7 Hz, 1H), 0.36 (dt, J=11.9, 4.7 Hz, 2H), 0.29-0.20 (m, 2H); $^{13}$C NMR (101 MHz, MeOD) δ 178.31, 171.09, 136.26, 86.31, 57.22, 52.69, 48.74, 47.41, 44.23, 36.90, 36.82, 30.84, 29.03, 28.35, 27.83, 19.43, 13.21, 11.20, 10.90, 9.56.

Synthesis Method of Compound (47):

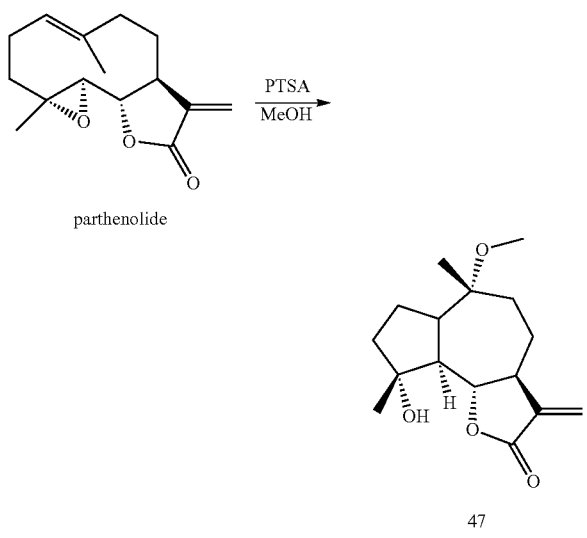

Dissolve parthenolide (566.2 mg, 1.99 mmol) in methanol and add p-toluenesulfonic acid (687.5 mg, 4.0 mmol). Place the reaction system at room temperature and stir it overnight. Neutralize the reaction mixture with Na$_2$HPO$_4$ (568 mg, 4.0 mmol), then extract it with CH$_2$Cl$_2$, collect the organic layer and dry it with Na$_2$SO$_4$, then filter it and evaporate the organic solvent at reduced pressure with rotary evaporator, purify the remaining product with silica gel column to get Compound 47. $^1$H NMR (CDCl$_3$, 400 MHz) δ 6.12 (d, J=2.8 Hz, 1H), 5.44 (s, 1H), 4.13 (t, J=9.6 Hz, 1H), 3.12 (d, J=2.8 Hz, 3H), 2.79 (t, J=11.8 Hz, 2H), 2.26 (t, J=9.6 Hz, 1H), 2.11-2.08 (m, 1H), 1.98-1.62 (m, 6H), 1.52-1.45 (m, 1H), 1.31-1.37 (m, 4H), 1.09 (s, 3H); $^{13}$C NMR (CDCl$_3$, 100 MHz) δ 169.5, 138.9, 119.8, 82.5, 80.3, 77.9, 55.3, 48.1, 46.4, 45.7, 35.3, 38.7, 25.2, 24.1, 22.5, 14.0.

Synthesis Method of Compound (48 and 49):

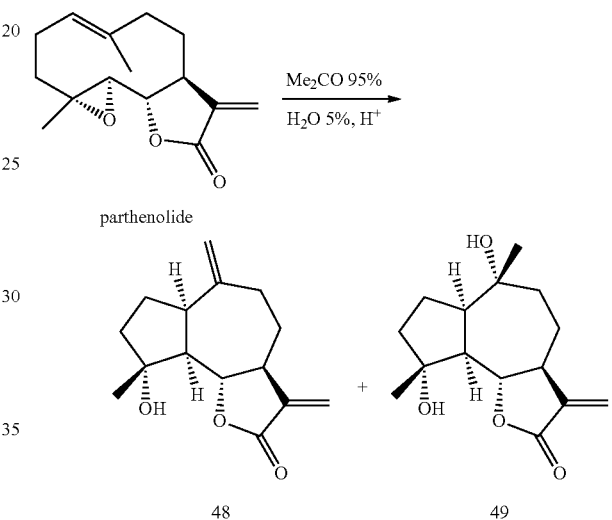

Add amberlyst 15 (12.88 g) into parthenolide (1.03 g, 4.1 mmol) solution and the solution of acetone: water (95:5), place the reaction system to react at room temperature and monitor the reaction with TLC until the raw materials disappear. After the reaction is completed, remove the solvent through rotary evaporation, dissolve the remaining substances in CH$_2$Cl$_2$, and dry with Na$_2$SO$_4$. Filter the product and remove the solvent through rotary evaporation, then purify it through silica gel column to get the products 48 and 49.

Compound 48: $^1$H NMR (CDCl$_3$, 400 MHz) δ 6.12 (d, J=3.2 Hz, 1H), 5.44 (d, J=3.2 Hz, 1H), 4.92 (s, 1H), 4.88 (s, 1H), 4.03-3.94 (m, 1H), 2.93 (dd, J=11.6, 8.8 Hz, 1H), 2.71-2.65 (m, 1H), 2.61-2.56 (m, 1H), 2.29 (t, J=12 Hz, 1H), 2.22-2.16 (m, 1H), 1.85-1.74 (m, 3H), 1.72-1.69 (m, 31H), 1.34-1.26 (m, 3H), 1.23 (s, 3H); $^{13}$C NMR (CDCl$_3$, 100 MHz) δ 169.6, 147.8, 138.5, 120.5, 112.4, 83.8, 79.5, 55.4, 47.0, 43.7, 40.0, 38.9, 31.2, 25.9, 23.6.

Compound 49: $^1$H NMR (CDCl$_3$, 400 MHz) δ 6.24 (d, J=3.6 Hz, 1H), 5.56 (d, J=3.2 Hz, 1H), 4.26 (s, 1H), 9.6 (s, 1H), 2.75-2.62 (m, 1H), 2.40 (dd, J=11.6, 12.4 Hz, 1H), 2.20-2.14 (m, 1H), 2.08-2.56 (m, 1H), 2.03 (t, J=12 Hz, 1H), 1.76-1.60 (m, 1H), 1.52-1.45 (m, 3H), 1.36-1.69 (m, 3H), 1.28-1.26 (m, 3H), 1.25 (s, 3H); $^{13}$C NMR (CDCl$_1$, 400 MHz) δ 169.6, 138.4, 120.4, 82.7, 80.0, 74.7, 55.2, 49.6, 47.1, 39.3, 25.2, 24.9, 24.1, 23.4, 20.6.

Preparation of Compound 50:

Dissolve Martin's sulfurane (382 mg, 0.57 mmol) in 2 mL $CH_2Cl_2$, under the protection of Ar, slowly drip 4 mL $CH_2Cl_2$ solution of Compound 24. The reaction mixture solution changes gradually to yellow color, then stir it 24 hours, after the reactive raw materials disappear completely, remove the solvent through rotary evaporation at reduced pressure to get yellow oily substance, and then purify the crude product with silica gel column to get Compound 50. $^1$H NMR (CDCl$_3$, 400 MHz) δ 6.14 (d, J=3.2 Hz, 1H), 5.57 (s, 1H), 5.41 (d, J=3.2 Hz, 1H), 4.00 (t, J=10.4 Hz, 1H), 2.93 (br.d, J=10.8 Hz, 1H), 2.77 (br.d, J=17.6 Hz, 1H), 2.27-2.12 (m, 3H), 2.03 (m, 1H), 1.9 7 (br s, 3H), 1.84 (br.d, J=14.0 Hz, 1H), 1.48 (m, 1H), 1.35 (s, 3H); $^{13}$C NMR (CDCl$_3$, 400 MHz) δ 170.6, 140.7, 139.2, 125.0, 118.4, 83.0, 72.6, 62.8, 52.9, 51.2, 39.8, 33.6, 22.9, 21.6, 18.4.

Embodiment 2: Test of Anti-rheumatoid Arthritis Activity of Compound 1-50

In the field of anti-rheumatoid arthritis drugs, there are many literatures reporting the effects of drug ingredients on synoviocyte to secrete TNF-α, PGE2 and IL-1β and using the data from animal test to investigate the therapeutic effect of drug on RA. These studies include [1] Dahong Ju, Hlongwei Jia and Hao Wu, et al. Effects of Cervus and Cucumis Polypeptide Injection on Activity of Antibodies TNF-α, IL-6 and C II of Immune Arthritis Rat Serum Induced by C II, China Journal of Basic Medicine in Traditional Chinese Medicine, 2003, 9 (11); 17. [2] JinHua He, Qinghua Liang, Huasheng Zhang, et al. Effects of Bizhongxiao Decoction on Plasma TNF-α of Experimental Arthritis Rats, Bulletin of Hunan Medical University, 2002, 27(5): 524. [3] Qingchun Huang, Shengpeng Zhang, Qiuying Xu. Effects of Compound Danshen on Synoviocyte's Secretion and Tumor Necrosis Factor of Rat Model Induced by Type II Collagen, 2001, 5 (10): 54-55. [4] Zhigang Zheng, Cytokine and Its Test Method and Clinical Significance, Shaanxi J Med Lab Sci, 2001, 16(2): 59. [5] Jun Zhou, Suping Fang, Yun Qi, et al. Effects of Kakkonto on Inflammatory Mediator in Joint Fluid of Adjuvant Induced Arthritis Rats, 2001, 7(3): 29. [6] Ji Ma, Bingjiu Lu, Xiaoming Zhu, et al. Study on Pharmacodynamics of Tongbi Keli to Treat Rheumatoid Arthritis, 2001, 19(6): 734. [7]Jiang Zhu, Wenli Xie, Yuzhnag Jin, et al. Effects of Gardenia on Serum IL-1β and TNF-α of Rheumatoid Arthritis Rats, Chinese Traditional Patent Medicine, 2005, 27(7): 801. [8]Qingchun Huang, Shengpeng Zhang, Weiyi Huang, et al. Effects of Compound Danshen Injection on Expression of IL-1βmRNA of CIA Rat Synoviocyte, Journal of Anhui Traditional Chinese Medical College, 2002, 21(5): 39-41.

Take Compound 1-50 prepared as per the method according to the present invention and employ the method provided in Reference [3] to prepare model, group drugs and prepare culture supernatant of rat synoviocyte.

Employ the method provided in Reference [3] to investigate the effects of the test compounds on the synoviocyte to secrete TNF-α and PGE2. Employ the method provided in Reference [8] to investigate the effects of the test compounds on the synoviocyte to secrete IL-1β.

The experimental data of the test compound 1-50 at a dose of 30 mg/kg.2d as well as the normal control and NaCl group are as follows:

TABLE 1

Content of TNF-α in culture supernatant of synoviocyte (x ± s, ng/mL)

| Group | TNF-α |
|---|---|
| Normal control | 0.38 ± 0.027 |
| NaCl | 0.74 ± 0.098 |
| Compound 1 | 0.41 ± 0.076 |
| Compound 2 | 0.45 ± 0.052 |
| Compound 3 | 0.55 ± 0.042 |
| Compound 4 | 0.56 ± 0.064 |
| Compound 5 | 0.49 ± 0.056 |
| Compound 6 | 0.61 ± 0.072 |
| Compound 7 | 0.56 ± 0.044 |
| Compound 8 | 0.58 ± 0.053 |
| Compound 9 | 0.61 ± 0.065 |
| Compound 10 | 0.54 ± 0.055 |
| Compound 11 | 0.49 ± 0.076 |
| Compound 12 | 0.66 ± 0.043 |
| Compound 13 | 0.62 ± 0.056 |
| Compound 14 | 0.48 ± 0.055 |
| Compound 15 | 0.54 ± 0.045 |
| Compound 16 | 0.57 ± 0.073 |
| Compound 17 | 0.66 ± 0.077 |
| Compound 18 | 0.64 ± 0.072 |
| Compound 19 | 0.62 ± 0.056 |
| Compound 20 | 0.58 ± 0.045 |
| Compound 21 | 0.56 ± 0.034 |
| Compound 22 | 0.61 ± 0.082 |
| Compound 23 | 0.63 ± 0.063 |
| Compound 24 | 0.54 ± 0.057 |
| Compound 25 | 0.58 ± 0.056 |
| Compound 26 | 0.59 ± 0.051 |
| Compound 27 | 0.54 ± 0.066 |
| Compound 28 | 0.47 ± 0.056 |
| Compound 29 | 0.66 ± 0.046 |
| Compound 30 | 0.65 ± 0.057 |
| Compound 31 | 0.62 ± 0.056 |
| Compound 32 | 0.64 ± 0.044 |
| Compound 33 | 0.63 ± 0.054 |
| Compound 34 | 0.54 ± 0.067 |
| Compound 35 | 0.57 ± 0.057 |
| Compound 36 | 0.66 ± 0.045 |
| Compound 37 | 0.59 ± 0.035 |
| Compound 38 | 0.67 ± 0.045 |
| Compound 39 | 0.52 ± 0.056 |
| Compound 40 | 0.48 ± 0.078 |
| Compound 41 | 0.45 ± 0.056 |
| Compound 42 | 0.58 ± 0.055 |
| Compound 43 | 0.55 ± 0.045 |
| Compound 44 | 0.54 ± 0.071 |
| Compound 45 | 0.49 ± 0.056 |
| Compound 46 | 0.56 ± 0.034 |
| Compound 47 | 0.64 ± 0.062 |
| Compound 48 | 0.62 ± 0.054 |
| Compound 49 | 0.65 ± 0.046 |
| Compound 50 | 0.52 ± 0.064 |

TABLE 2

Content of IL-1β in culture supernatant of synoviocyte (x ± s, ng/mL)

| Group | IL-1β |
|---|---|
| Normal control | 0.16 ± 0.034 |
| NaCl | 0.49 ± 0.136 |
| Compound 1 | 0.26 ± 0.042 |
| Compound 2 | 0.28 ± 0.045 |
| Compound 3 | 0.36 ± 0.039 |
| Compound 4 | 0.42 ± 0.064 |
| Compound 5 | 0.38 ± 0.062 |
| Compound 6 | 0.36 ± 0.054 |
| Compound 7 | 0.39 ± 0.058 |
| Compound 8 | 0.41 ± 0.051 |
| Compound 9 | 0.45 ± 0.064 |
| Compound 10 | 0.42 ± 0.069 |
| Compound 11 | 0.39 ± 0.081 |
| Compound 12 | 0.38 ± 0.069 |
| Compound 13 | 0.37 ± 0.062 |

TABLE 2-continued

Content of IL-1β in culture supernatant of synoviocyte (x ± s, ng/mL)

| Group | IL-1β |
|---|---|
| Compound 14 | 0.36 ± 0.054 |
| Compound 15 | 0.41 ± 0.051 |
| Compound 16 | 0.34 ± 0.039 |
| Compound 17 | 0.37 ± 0.065 |
| Compound 18 | 0.39 ± 0.029 |
| Compound 19 | 0.42 ± 0.091 |
| Compound 20 | 0.34 ± 0.056 |
| Compound 21 | 0.36 ± 0.057 |
| Compound 22 | 0.34 ± 0.038 |
| Compound 23 | 0.36 ± 0.065 |
| Compound 24 | 0.37 ± 0.051 |
| Compound 25 | 0.39 ± 0.067 |
| Compound 26 | 0.42 ± 0.052 |
| Compound 27 | 0.41 ± 0.047 |
| Compound 28 | 0.31 ± 0.067 |
| Compound 29 | 0.34 ± 0.039 |
| Compound 30 | 0.38 ± 0.049 |
| Compound 31 | 0.39 ± 0.051 |
| Compound 32 | 0.37 ± 0.047 |
| Compound 33 | 0.41 ± 0.052 |
| Compound 34 | 0.35 ± 0.059 |
| Compound 35 | 0.41 ± 0.056 |
| Compound 36 | 0.29 ± 0.064 |
| Compound 37 | 0.31 ± 0.037 |
| Compound 38 | 0.35 ± 0.062 |
| Compound 39 | 0.34 ± 0.095 |
| Compound 40 | 0.31 ± 0.061 |
| Compound 41 | 0.41 ± 0.054 |
| Compound 42 | 0.36 ± 0.059 |
| Compound 43 | 0.43 ± 0.062 |
| Compound 44 | 0.35 ± 0.069 |
| Compound 45 | 0.38 ± 0.039 |
| Compound 46 | 0.36 ± 0.067 |
| Compound 47 | 0.34 ± 0.058 |
| Compound 48 | 0.38 ± 0.046 |
| Compound 49 | 0.39 ± 0.075 |
| Compound 50 | 0.34 ± 0.061 |

TABLE 3

Content of PGE2 in culture supernatant of synoviocyte (x ± s, ng/mL)

| Group | IL-1β |
|---|---|
| Normal control | 8.34 ± 1.29 |
| NaCl | 32.44 ± 10.32 |
| Compound 1 | 15.24 ± 1.77 |
| Compound 2 | 18.58 ± 0.98 |
| Compound 3 | 26.96 ± 1.59 |
| Compound 4 | 24.49 ± 2.67 |
| Compound 5 | 25.67 ± 4.23 |
| Compound 6 | 26.75 ± 1.69 |
| Compound 7 | 22.82 ± 2.67 |
| Compound 8 | 23.69 ± 1.25 |
| Compound 9 | 27.92 ± 2.67 |
| Compound 10 | 25.67 ± 7.12 |
| Compound 11 | 26.38 ± 3.15 |
| Compound 12 | 24.59 ± 2.35 |
| Compound 13 | 25.61 ± 0.98 |
| Compound 14 | 26.44 ± 1.26 |
| Compound 15 | 24.39 ± 2.38 |
| Compound 16 | 27.61 ± 4.21 |
| Compound 17 | 28.95 ± 3.24 |
| Compound 18 | 20.62 ± 2.47 |
| Compound 19 | 26.45 ± 5.21 |
| Compound 20 | 27.38 ± 1.39 |
| Compound 21 | 19.59 ± 3.25 |
| Compound 22 | 24.69 ± 4.19 |
| Compound 23 | 21.71 ± 2.32 |
| Compound 24 | 23.63 ± 1.35 |
| Compound 25 | 26.48 ± 2.57 |
| Compound 26 | 25.61 ± 5.41 |
| Compound 27 | 24.75 ± 2.66 |

TABLE 3-continued

Content of PGE2 in culture supernatant of synoviocyte (x ± s, ng/mL)

| Group | IL-1β |
|---|---|
| Compound 28 | 18.92 ± 1.98 |
| Compound 29 | 27.64 ± 2.37 |
| Compound 30 | 25.37 ± 4.21 |
| Compound 31 | 24.41 ± 1.65 |
| Compound 32 | 22.75 ± 4.25 |
| Compound 33 | 26.64 ± 2.67 |
| Compound 34 | 24.61 ± 3.24 |
| Compound 35 | 21.54 ± 1.32 |
| Compound 36 | 25.64 ± 2.14 |
| Compound 37 | 27.94 ± 2.69 |
| Compound 38 | 19.67 ± 3.14 |
| Compound 39 | 28.35 ± 2.15 |
| Compound 40 | 25.34 ± 3.57 |
| Compound 41 | 26.63 ± 1.59 |
| Compound 42 | 22.58 ± 4.21 |
| Compound 43 | 24.64 ± 3.95 |
| Compound 44 | 22.14 ± 2.87 |
| Compound 45 | 23.26 ± 3.49 |
| Compound 46 | 24.74 ± 2.64 |
| Compound 47 | 27.95 ± 3.67 |
| Compound 48 | 26.65 ± 2.45 |
| Compound 49 | 24.25 ± 1.94 |
| Compound 50 | 19.83 ± 1.78 |

The present invention selects the rat as the animal model for human RA and employs the method of primary culture of synoviocyte to observe the effects of Compounds 1-50 on the synoviocyte to secrete TNF-α, PGE2 and IL-1β. The result indicates that Compounds 1-50 all can obviously reduce the content of TNF-α, PGE2 and IL-1β of both large dose group and small dose group, to realize the functions of alleviating damages to bone and cartilage as well as restoring the action function of joint and realize the effect of RA treatment.

Embodiment 3: Test of Compound Activity to Inhibit Cancer Stem Cell

Take fresh or cryopreserved clinical specimen (acute myelogenous leukemia (AML, marker is $CD34^+/CD38^+$), chronic myelogenous leukemia (CML, Ph+/CD34+/CXCR4+), chronic lymphocytic leukemia (CLL,CD133+/CD19−/CD38−), skin cancer (CD34+), breast cancer (CD44+/CD24−/ESA+), ovarian cancer (CD44+/CD117+), brain tumor (CD133+) prostate cancer (CD44+/CD24−), head-neck squamous cell carcinoma (CD44+), laryngeal cancer (CD133+), pancreatic cancer (ESA+/CD44+/CD24+), retinoblastoma (ABCG2/ALDH1), Children hepatoblastoma (CD34+/THY1+/c-kit+), liver cancer (CD133+), malignant melanoma (CD133+), colorectal cancer (Ep-CAM$^{high}$/CD44+), colon adenocarcinoma (CD44$^{high}$), glioma (ABCG-2/BCRP1), gastrointestinal tumor (ABCG-2/BCRP1), nasopharynx cancer (ABCG2), brain glioma (Dlk-1/Pref-1), gastric cancer (CD45+), lung adenocarcinoma (Sca-1/CD45−/Pecam−/CD34+), lung cancer (CD133+ CD34+CD44+)) of patient. Take the acute myelogenous leukemia as the example, conduct density gradient centrifugation with Ficoll and take out the middle mononuclear cells, re-suspend it with serum-free IMDM after centrifuged. Adjust the concentration of cells into $1\times10^6$/mL and lay 24-well plate with 1 mL in each well, and then treat 18 hours with the compound to select with corresponding concentration. Collect the cells and centrifuge them at 1500 rps for 8 minutes, re-suspend the precipitation with 100 ml, mark the antibodies related to leukemia stem cell, avoid light to incubate 30 minutes at room temperature and then centrifuge it at 1500 rps, then wash away the unbound antibody $CD34^+CD38^+$. Re-suspend it with 100 μl 1× Binding Buffer and add respectively 5 μl Annexin V-FITC and PI, then avoid light to incubate 15 minutes before add 200 μl 1× Binding Buffer, then use flow cytometry to examine the marked apoptosis within one hour.

TABLE 4

Survival rate (%) of cancer cells, cancer stem cells and normal cells after test compound is added

| Compound | Cells | 10.0 μM Stem cells | 10.0 μM All cells (Stem cells and ordinary cells) | 20.0 μM Stem cells | 20.0 μM All cells (Stem cells and ordinary cells) |
|---|---|---|---|---|---|
| Compound 1 | AML | 34 | 55 | 24 | 45 |
| | CML | 55 | 65 | 26 | 39 |
| | CLL | 44 | 55 | 32 | 46 |
| | Skin cancer | 57 | 59 | 23 | 28 |
| | Breast cancer | 65 | 69 | 42 | 55 |
| | Ovarian cancer | 67 | 78 | 45 | 59 |
| | Brain tumor | 78 | 88 | 69 | 72 |
| | Prostate cancer | 34 | 46 | 21 | 26 |
| | Head and neck squamous cell carcinomas | 60 | 67 | 37 | 48 |
| | Laryngeal cancer | 65 | 75 | 54 | 64 |
| | Pancreatic cancer | 54 | 64 | 36 | 48 |
| | Retinoblastoma | 55 | 64 | 34 | 54 |
| | Children hepatoblastoma | 46 | 54 | 29 | 37 |
| | Liver cancer | 55 | 68 | 36 | 48 |
| | Malignant melanoma | 72 | 85 | 56 | 69 |
| | Colorectal cancer | 65 | 78 | 45 | 67 |
| | Colon adenocarcinoma | 43 | 56 | 24 | 39 |
| | Glioma | 77 | 87 | 66 | 72 |
| | Gastrointestinal tumor | 56 | 62 | 41 | 51 |
| | Nasopharynx cancer | 25 | 34 | 17 | 28 |
| | Brain glioma | 65 | 69 | 37 | 47 |
| | Gastric cancer | 45 | 56 | 27 | 37 |
| | Lung adenocarcinoma | 36 | 47 | 24 | 34 |
| | Lung cancer | 45 | 53 | 19 | 26 |
| | Normal cells | 88 | 91 | 91 | 93 |
| Compound 2 | AML | 38 | 54 | 34 | 46 |
| | CML | 41 | 49 | 36 | 41 |
| | CLL | 48 | 57 | 37 | 49 |
| | Skin cancer | 36 | 42 | 29 | 37 |
| | Breast cancer | 44 | 57 | 37 | 51 |
| | Ovarian cancer | 37 | 48 | 35 | 41 |
| | Brain tumor | 56 | 64 | 44 | 59 |
| | Prostate cancer | 41 | 45 | 31 | 42 |
| | Head and neck squamous cell carcinomas | 54 | 67 | 37 | 48 |
| | Laryngeal cancer | 55 | 75 | 54 | 64 |
| | Pancreatic cancer | 47 | 69 | 59 | 64 |
| | Retinoblastoma | 52 | 62 | 44 | 49 |
| | Children hepatoblastoma | 57 | 53 | 37 | 41 |
| | Liver cancer | 64 | 62 | 41 | 58 |
| | Malignant melanoma | 71 | 75 | 66 | 69 |
| | Colorectal cancer | 56 | 68 | 45 | 57 |
| | Colon adenocarcinoma | 48 | 56 | 44 | 51 |
| | Glioma | 67 | 77 | 66 | 73 |
| | Gastrointestinal tumor | 46 | 52 | 41 | 47 |
| | Nasopharynx cancer | 37 | 44 | 27 | 29 |
| | Brain glioma | 62 | 68 | 47 | 53 |
| | Gastric cancer | 41 | 46 | 37 | 47 |
| | Lung adenocarcinoma | 64 | 73 | 54 | 64 |
| | Lung cancer | 41 | 52 | 34 | 46 |
| | Normal cells | 91 | 92 | 89 | 91 |
| Compound 5 | AML | 39 | 47 | 34 | 41 |
| | CML | 45 | 55 | 36 | 42 |
| | CLL | 37 | 52 | 34 | 44 |
| | Skin cancer | 55 | 61 | 43 | 49 |
| | Breast cancer | 55 | 64 | 43 | 51 |
| | Ovarian cancer | 57 | 68 | 35 | 45 |
| | Brain tumor | 77 | 87 | 66 | 72 |
| | Prostate cancer | 56 | 62 | 41 | 51 |
| | Head and neck squamous cell carcinomas | 45 | 54 | 37 | 48 |
| | Laryngeal cancer | 65 | 69 | 37 | 47 |
| | Pancreatic cancer | 45 | 56 | 27 | 37 |
| | Retinoblastoma | 62 | 68 | 47 | 56 |
| | Children hepatoblastoma | 52 | 56 | 47 | 51 |
| | Liver cancer | 49 | 57 | 42 | 52 |
| | Malignant melanoma | 55 | 58 | 45 | 49 |
| | Colorectal cancer | 65 | 78 | 45 | 67 |
| | Colon adenocarcinoma | 43 | 56 | 24 | 39 |
| | Glioma | 77 | 87 | 66 | 72 |
| | Gastrointestinal tumor | 56 | 62 | 41 | 51 |
| | Nasopharynx cancer | 25 | 34 | 17 | 28 |
| | Brain glioma | 65 | 69 | 37 | 47 |
| | Gastric cancer | 45 | 56 | 27 | 37 |
| | Lung adenocarcinoma | 36 | 47 | 24 | 34 |
| | Lung cancer | 45 | 53 | 19 | 26 |
| | Normal cells | 95 | 96 | 93 | 94 |
| Compound 8 | AML | 34 | 55 | 24 | 45 |
| | CML | 55 | 65 | 26 | 39 |
| | CLL | 44 | 55 | 32 | 46 |
| | Skin cancer | 57 | 59 | 23 | 28 |
| | Breast cancer | 65 | 69 | 42 | 55 |
| | Ovarian cancer | 67 | 78 | 45 | 59 |
| | Brain tumor | 78 | 88 | 69 | 72 |
| | Prostate cancer | 34 | 46 | 21 | 26 |
| | Head and neck squamous cell carcinomas | 60 | 67 | 37 | 48 |
| | Laryngeal cancer | 52 | 58 | 39 | 47 |
| | Pancreatic cancer | 62 | 75 | 56 | 68 |
| | Retinoblastoma | 62 | 68 | 45 | 57 |
| | Children hepatoblastoma | 48 | 61 | 34 | 43 |
| | Liver cancer | 52 | 58 | 39 | 47 |
| | Malignant melanoma | 62 | 75 | 56 | 68 |
| | Colorectal cancer | 57 | 59 | 23 | 28 |
| | Colon adenocarcinoma | 65 | 69 | 42 | 55 |
| | Glioma | 67 | 78 | 45 | 59 |
| | Gastrointestinal tumor | 78 | 88 | 69 | 72 |
| | Nasopharynx cancer | 34 | 46 | 21 | 26 |
| | Brain glioma | 60 | 67 | 37 | 48 |
| | Gastric cancer | 65 | 75 | 54 | 64 |
| | Lung adenocarcinoma | 62 | 68 | 47 | 56 |
| | Lung cancer | 52 | 56 | 47 | 51 |
| | Normal cells | 95 | 96 | 89 | 94 |
| Compound 11 | AML | 55 | 58 | 45 | 49 |
| | CML | 65 | 71 | 49 | 59 |
| | CLL | 45 | 55 | 34 | 43 |
| | Skin cancer | 55 | 65 | 26 | 39 |
| | Breast cancer | 44 | 55 | 32 | 46 |
| | Ovarian cancer | 57 | 59 | 23 | 28 |
| | Brain tumor | 45 | 69 | 42 | 55 |

TABLE 4-continued

Survival rate (%) of cancer cells, cancer stem cells and normal cells after test compound is added

| Compound | Cells | 10.0 μM Stem cells | 10.0 μM All cells (Stem cells and ordinary cells) | 20.0 μM Stem cells | 20.0 μM All cells (Stem cells and ordinary cells) |
|---|---|---|---|---|---|
| | Prostate cancer | 45 | 67 | 37 | 56 |
| | Head and neck squamous cell carcinomas | 65 | 69 | 47 | 59 |
| | Laryngeal cancer | 61 | 72 | 53 | 62 |
| | Pancreatic cancer | 47 | 58 | 37 | 46 |
| | Retinoblastoma | 52 | 61 | 44 | 56 |
| | Children hepatoblastoma | 45 | 53 | 39 | 47 |
| | Liver cancer | 52 | 58 | 39 | 47 |
| | Malignant melanoma | 62 | 75 | 56 | 68 |
| | Colorectal cancer | 62 | 68 | 45 | 57 |
| | Colon adenocarcinoma | 48 | 61 | 34 | 43 |
| | Glioma | 67 | 77 | 56 | 62 |
| | Gastrointestinal tumor | 49 | 57 | 40 | 52 |
| | Nasopharynx cancer | 45 | 54 | 34 | 48 |
| | Brain glioma | 62 | 68 | 47 | 56 |
| | Gastric cancer | 52 | 56 | 47 | 51 |
| | Lung adenocarcinoma | 49 | 57 | 42 | 52 |
| | Lung cancer | 55 | 58 | 45 | 49 |
| | Normal cells | 92 | 96 | 90 | 93 |
| Compound 13 | AML | 45 | 55 | 34 | 43 |
| | CML | 55 | 65 | 26 | 39 |
| | CLL | 44 | 55 | 32 | 46 |
| | Skin cancer | 57 | 59 | 23 | 28 |
| | Breast cancer | 45 | 69 | 42 | 55 |
| | Ovarian cancer | 67 | 78 | 45 | 59 |
| | Brain tumor | 78 | 88 | 69 | 72 |
| | Prostate cancer | 34 | 46 | 21 | 26 |
| | Head and neck squamous cell carcinomas | 60 | 67 | 37 | 48 |
| | Laryngeal cancer | 65 | 75 | 54 | 64 |
| | Pancreatic cancer | 54 | 64 | 46 | 52 |
| | Retinoblastoma | 35 | 44 | 24 | 44 |
| | Children hepatoblastoma | 46 | 54 | 29 | 37 |
| | Liver cancer | 55 | 68 | 36 | 48 |
| | Malignant melanoma | 72 | 85 | 56 | 69 |
| | Colorectal cancer | 65 | 78 | 45 | 67 |
| | Colon adenocarcinoma | 43 | 56 | 24 | 39 |
| | Glioma | 77 | 87 | 66 | 72 |
| | Gastrointestinal tumor | 56 | 62 | 41 | 51 |
| | Nasopharynx cancer | 25 | 34 | 17 | 28 |
| | Brain glioma | 65 | 69 | 37 | 47 |
| | Gastric cancer | 41 | 55 | 37 | 47 |
| | Lung adenocarcinoma | 57 | 68 | 44 | 54 |
| | Lung cancer | 62 | 73 | 45 | 61 |
| | Normal cells | 92 | 95 | 87 | 93 |
| Compound 14 | AML | 42 | 67 | 37 | 56 |
| | CML | 65 | 69 | 47 | 59 |
| | CLL | 61 | 72 | 53 | 62 |
| | Skin cancer | 47 | 58 | 37 | 46 |
| | Breast cancer | 52 | 61 | 44 | 56 |
| | Ovarian cancer | 45 | 53 | 39 | 47 |
| | Brain tumor | 55 | 64 | 43 | 51 |
| | Prostate cancer | 57 | 68 | 35 | 45 |
| | Head and neck squamous cell carcinomas | 76 | 87 | 66 | 72 |
| | Laryngeal cancer | 56 | 62 | 41 | 51 |
| | Pancreatic cancer | 49 | 57 | 40 | 52 |
| | Retinoblastoma | 45 | 54 | 34 | 49 |
| | Children hepatoblastoma | 63 | 68 | 47 | 56 |
| | Liver cancer | 52 | 56 | 46 | 51 |
| | Malignant melanoma | 57 | 69 | 35 | 45 |
| | Colorectal cancer | 62 | 68 | 45 | 57 |
| | Colon adenocarcinoma | 48 | 61 | 34 | 43 |
| | Glioma | 67 | 77 | 56 | 63 |
| | Gastrointestinal tumor | 55 | 65 | 26 | 39 |
| | Nasopharynx cancer | 44 | 54 | 32 | 46 |
| | Brain glioma | 57 | 59 | 23 | 28 |
| | Gastric cancer | 45 | 69 | 42 | 55 |
| | Lung adenocarcinoma | 47 | 69 | 59 | 64 |
| | Lung cancer | 52 | 62 | 44 | 49 |
| | Normal cells | 93 | 94 | 91 | 93 |
| Compound 21 | AML | 66 | 75 | 47 | 56 |
| | CML | 75 | 82 | 56 | 69 |
| | CLL | 51 | 63 | 48 | 62 |
| | Skin cancer | 56 | 64 | 47 | 57 |
| | Breast cancer | 62 | 72 | 55 | 66 |
| | Ovarian cancer | 56 | 64 | 49 | 57 |
| | Brain tumor | 65 | 75 | 54 | 62 |
| | Prostate cancer | 68 | 77 | 57 | 65 |
| | Head and neck squamous cell carcinomas | 75 | 86 | 66 | 82 |
| | Laryngeal cancer | 66 | 73 | 52 | 61 |
| | Pancreatic cancer | 57 | 66 | 50 | 62 |
| | Retinoblastoma | 56 | 65 | 47 | 59 |
| | Children hepatoblastoma | 74 | 81 | 57 | 66 |
| | Liver cancer | 64 | 77 | 55 | 61 |
| | Malignant melanoma | 59 | 69 | 45 | 56 |
| | Colorectal cancer | 73 | 78 | 58 | 67 |
| | Colon adenocarcinoma | 58 | 71 | 44 | 56 |
| | Glioma | 78 | 87 | 67 | 78 |
| | Gastrointestinal tumor | 64 | 75 | 46 | 58 |
| | Nasopharynx cancer | 55 | 65 | 42 | 56 |
| | Brain glioma | 68 | 79 | 53 | 68 |
| | Gastric cancer | 56 | 67 | 45 | 55 |
| | Lung adenocarcinoma | 58 | 67 | 49 | 64 |
| | Lung cancer | 63 | 74 | 54 | 68 |
| | Normal cells | 94 | 95 | 92 | 94 |
| Compound 23 | AML | 85 | 92 | 72 | 84 |
| | CML | 87 | 91 | 71 | 79 |
| | CLL | 86 | 95 | 74 | 85 |
| | Skin cancer | 85 | 95 | 75 | 87 |
| | Breast cancer | 84 | 89 | 74 | 86 |
| | Ovarian cancer | 87 | 91 | 75 | 84 |
| | Brain tumor | 85 | 89 | 73 | 85 |
| | Prostate cancer | 85 | 92 | 77 | 89 |
| | Head and neck squamous cell carcinomas | 84 | 91 | 78 | 88 |
| | Laryngeal cancer | 79 | 88 | 73 | 82 |
| | Pancreatic cancer | 87 | 90 | 77 | 86 |
| | Retinoblastoma | 82 | 91 | 74 | 85 |
| | Children hepatoblastoma | 85 | 93 | 79 | 86 |
| | Liver cancer | 82 | 88 | 79 | 87 |
| | Malignant melanoma | 82 | 89 | 76 | 86 |
| | Colorectal cancer | 79 | 88 | 72 | 81 |
| | Colon adenocarcinoma | 88 | 91 | 81 | 89 |

TABLE 4-continued

Survival rate (%) of cancer cells, cancer stem cells and normal cells after test compound is added

| Compound | Cells | 10.0 μM Stem cells | 10.0 μM All cells (Stem cells and ordinary cells) | 20.0 μM Stem cells | 20.0 μM All cells (Stem cells and ordinary cells) |
|---|---|---|---|---|---|
| | Glioma | 87 | 94 | 76 | 87 |
| | Gastrointestinal tumor | 91 | 94 | 82 | 88 |
| | Nasopharynx cancer | 85 | 94 | 74 | 81 |
| | Brain glioma | 84 | 88 | 76 | 85 |
| | Gastric cancer | 82 | 86 | 77 | 84 |
| | Lung adenocarcinoma | 85 | 87 | 82 | 87 |
| | Lung cancer | 85 | 88 | 78 | 84 |
| | Normal cells | 93 | 96 | 92 | 95 |
| Compound 24 | AML | 48 | 59 | 39 | 48 |
| | CML | 51 | 69 | 46 | 51 |
| | CLL | 48 | 67 | 39 | 48 |
| | Skin cancer | 46 | 62 | 39 | 47 |
| | Breast cancer | 54 | 77 | 47 | 58 |
| | Ovarian cancer | 57 | 68 | 45 | 61 |
| | Brain tumor | 66 | 74 | 54 | 69 |
| | Prostate cancer | 61 | 75 | 51 | 62 |
| | Head and neck squamous cell carcinomas | 64 | 76 | 57 | 68 |
| | Laryngeal cancer | 65 | 75 | 55 | 66 |
| | Pancreatic cancer | 55 | 68 | 49 | 62 |
| | Retinoblastoma | 62 | 82 | 54 | 69 |
| | Children hepatoblastoma | 67 | 75 | 57 | 68 |
| | Liver cancer | 74 | 82 | 61 | 72 |
| | Malignant melanoma | 81 | 88 | 76 | 86 |
| | Colorectal cancer | 66 | 78 | 55 | 67 |
| | Colon adenocarcinoma | 58 | 66 | 49 | 57 |
| | Glioma | 69 | 78 | 60 | 74 |
| | Gastrointestinal tumor | 56 | 72 | 51 | 62 |
| | Nasopharynx cancer | 57 | 64 | 48 | 59 |
| | Brain glioma | 52 | 65 | 42 | 53 |
| | Gastric cancer | 51 | 66 | 39 | 48 |
| | Lung adenocarcinoma | 68 | 78 | 55 | 64 |
| | Lung cancer | 61 | 72 | 54 | 66 |
| | Normal cells | 92 | 93 | 90 | 92 |
| Compound 25 | AML | 35 | 47 | 26 | 44 |
| | CML | 57 | 64 | 36 | 49 |
| | CLL | 46 | 57 | 34 | 45 |
| | Skin cancer | 55 | 66 | 43 | 58 |
| | Breast cancer | 66 | 74 | 52 | 65 |
| | Ovarian cancer | 64 | 76 | 55 | 67 |
| | Brain tumor | 72 | 83 | 66 | 73 |
| | Prostate cancer | 44 | 56 | 31 | 44 |
| | Head and neck squamous cell carcinomas | 56 | 67 | 47 | 58 |
| | Laryngeal cancer | 64 | 74 | 53 | 64 |
| | Pancreatic cancer | 54 | 64 | 36 | 48 |
| | Retinoblastoma | 55 | 64 | 34 | 54 |
| | Children hepatoblastoma | 44 | 53 | 39 | 47 |
| | Liver cancer | 52 | 65 | 46 | 54 |
| | Malignant melanoma | 62 | 81 | 54 | 66 |
| | Colorectal cancer | 62 | 76 | 55 | 66 |
| | Colon adenocarcinoma | 42 | 55 | 35 | 49 |
| | Glioma | 71 | 83 | 65 | 74 |
| | Gastrointestinal tumor | 54 | 63 | 44 | 52 |
| | Nasopharynx cancer | 45 | 54 | 37 | 48 |
| | Brain glioma | 62 | 74 | 47 | 58 |
| | Gastric cancer | 43 | 54 | 37 | 47 |
| | Lung adenocarcinoma | 46 | 57 | 34 | 46 |
| | Lung cancer | 42 | 54 | 29 | 37 |
| | Normal cells | 89 | 93 | 88 | 91 |
| Compound 26 | AML | 86 | 93 | 73 | 85 |
| | CML | 88 | 92 | 76 | 79 |
| | CLL | 84 | 93 | 74 | 85 |
| | Skin cancer | 86 | 94 | 75 | 87 |
| | Breast cancer | 85 | 89 | 74 | 86 |
| | Ovarian cancer | 86 | 91 | 75 | 84 |
| | Brain tumor | 84 | 89 | 73 | 85 |
| | Prostate cancer | 86 | 92 | 77 | 89 |
| | Head and neck squamous cell carcinomas | 84 | 91 | 78 | 88 |
| | Laryngeal cancer | 80 | 88 | 75 | 82 |
| | Pancreatic cancer | 86 | 90 | 77 | 86 |
| | Retinoblastoma | 82 | 91 | 74 | 85 |
| | Children hepatoblastoma | 85 | 93 | 79 | 86 |
| | Liver cancer | 82 | 89 | 79 | 87 |
| | Malignant melanoma | 82 | 88 | 76 | 86 |
| | Colorectal cancer | 79 | 87 | 72 | 81 |
| | Colon adenocarcinoma | 86 | 91 | 81 | 89 |
| | Glioma | 87 | 94 | 76 | 87 |
| | Gastrointestinal tumor | 87 | 93 | 82 | 88 |
| | Nasopharynx cancer | 85 | 94 | 74 | 81 |
| | Brain glioma | 84 | 88 | 76 | 85 |
| | Gastric cancer | 83 | 88 | 77 | 84 |
| | Lung adenocarcinoma | 85 | 91 | 82 | 87 |
| | Lung cancer | 82 | 88 | 78 | 84 |
| | Normal cells | 94 | 95 | 93 | 94 |
| Compound 27 | AML | 87 | 90 | 77 | 86 |
| | CML | 87 | 94 | 76 | 87 |
| | CLL | 87 | 93 | 82 | 88 |
| | Skin cancer | 85 | 94 | 74 | 81 |
| | Breast cancer | 84 | 88 | 76 | 85 |
| | Ovarian cancer | 83 | 88 | 77 | 84 |
| | Brain tumor | 87 | 94 | 76 | 87 |
| | Prostate cancer | 84 | 91 | 78 | 88 |
| | Head and neck squamous cell carcinomas | 81 | 87 | 75 | 83 |
| | Laryngeal cancer | 85 | 92 | 77 | 89 |
| | Pancreatic cancer | 86 | 93 | 78 | 92 |
| | Retinoblastoma | 85 | 94 | 80 | 86 |
| | Children hepatoblastoma | 82 | 88 | 79 | 87 |
| | Liver cancer | 86 | 90 | 77 | 86 |
| | Malignant melanoma | 82 | 91 | 74 | 85 |
| | Colorectal cancer | 85 | 93 | 79 | 86 |
| | Colon adenocarcinoma | 82 | 89 | 78 | 87 |
| | Glioma | 80 | 88 | 75 | 82 |
| | Gastrointestinal tumor | 86 | 90 | 77 | 86 |
| | Nasopharynx cancer | 82 | 91 | 74 | 85 |
| | Brain glioma | 84 | 91 | 78 | 88 |
| | Gastric cancer | 81 | 87 | 75 | 83 |
| | Lung adenocarcinoma | 82 | 89 | 76 | 86 |
| | Lung cancer | 79 | 88 | 72 | 81 |
| | Normal cells | 88 | 91 | 81 | 89 |
| Compound 28 | AML | 87 | 94 | 76 | 87 |
| | CML | 85 | 92 | 77 | 89 |
| | CLL | 82 | 91 | 73 | 87 |

TABLE 4-continued

Survival rate (%) of cancer cells, cancer stem cells and normal cells after test compound is added

| Compound | Cells | 10.0 μM Stem cells | 10.0 μM All cells (Stem cells and ordinary cells) | 20.0 μM Stem cells | 20.0 μM All cells (Stem cells and ordinary cells) |
|---|---|---|---|---|---|
| | Skin cancer | 84 | 91 | 78 | 88 |
| | Breast cancer | 81 | 87 | 75 | 83 |
| | Ovarian cancer | 85 | 88 | 79 | 85 |
| | Brain tumor | 82 | 91 | 73 | 87 |
| | Prostate cancer | 84 | 91 | 78 | 88 |
| | Head and neck squamous cell carcinomas | 81 | 87 | 75 | 83 |
| | Laryngeal cancer | 85 | 92 | 77 | 89 |
| | Pancreatic cancer | 86 | 93 | 78 | 92 |
| | Retinoblastoma | 84 | 90 | 80 | 85 |
| | Children hepatoblastoma | 85 | 92 | 77 | 89 |
| | Liver cancer | 82 | 91 | 73 | 87 |
| | Malignant melanoma | 84 | 91 | 78 | 88 |
| | Colorectal cancer | 81 | 87 | 75 | 83 |
| | Colon adenocarcinoma | 82 | 88 | 74 | 85 |
| | Glioma | 85 | 93 | 79 | 86 |
| | Gastrointestinal tumor | 82 | 88 | 76 | 89 |
| | Nasopharynx cancer | 85 | 92 | 77 | 89 |
| | Brain glioma | 82 | 89 | 76 | 86 |
| | Gastric cancer | 79 | 88 | 72 | 81 |
| | Lung adenocarcinoma | 88 | 91 | 81 | 89 |
| | Lung cancer | 87 | 94 | 76 | 87 |
| | Normal cells | 94 | 96 | 92 | 95 |
| Compound 29 | AML | 84 | 91 | 78 | 88 |
| | CML | 81 | 87 | 75 | 83 |
| | CLL | 85 | 88 | 79 | 85 |
| | Skin cancer | 82 | 91 | 73 | 87 |
| | Breast cancer | 79 | 88 | 72 | 81 |
| | Ovarian cancer | 88 | 91 | 81 | 89 |
| | Brain tumor | 87 | 94 | 76 | 87 |
| | Prostate cancer | 85 | 93 | 79 | 86 |
| | Head and neck squamous cell carcinomas | 82 | 88 | 74 | 85 |
| | Laryngeal cancer | 85 | 93 | 79 | 86 |
| | Pancreatic cancer | 82 | 88 | 76 | 89 |
| | Retinoblastoma | 85 | 92 | 77 | 89 |
| | Children hepatoblastoma | 85 | 92 | 77 | 89 |
| | Liver cancer | 85 | 92 | 77 | 89 |
| | Malignant melanoma | 82 | 91 | 73 | 87 |
| | Colorectal cancer | 84 | 91 | 78 | 88 |
| | Colon adenocarcinoma | 81 | 87 | 75 | 83 |
| | Glioma | 84 | 91 | 78 | 88 |
| | Gastrointestinal tumor | 81 | 87 | 75 | 83 |
| | Nasopharynx cancer | 85 | 88 | 79 | 85 |
| | Brain glioma | 82 | 89 | 76 | 86 |
| | Gastric cancer | 79 | 88 | 72 | 81 |
| | Lung adenocarcinoma | 88 | 91 | 81 | 89 |
| | Lung cancer | 87 | 94 | 76 | 87 |
| | Normal cells | 93 | 96 | 92 | 95 |
| Compound 35 | AML | 82 | 91 | 73 | 87 |
| | CML | 84 | 91 | 78 | 88 |
| | CLL | 81 | 87 | 75 | 83 |
| | Skin cancer | 85 | 92 | 77 | 89 |
| | Breast cancer | 86 | 93 | 78 | 92 |
| | Ovarian cancer | 84 | 91 | 78 | 88 |
| | Brain tumor | 81 | 87 | 75 | 83 |
| | Prostate cancer | 85 | 88 | 79 | 85 |
| | Head and neck squamous cell carcinomas | 82 | 91 | 73 | 87 |
| | Laryngeal cancer | 82 | 89 | 76 | 86 |
| | Pancreatic cancer | 79 | 88 | 72 | 81 |
| | Retinoblastoma | 88 | 91 | 81 | 89 |
| | Children hepatoblastoma | 87 | 94 | 76 | 87 |
| | Liver cancer | 84 | 89 | 74 | 86 |
| | Malignant melanoma | 87 | 91 | 75 | 84 |
| | Colorectal cancer | 82 | 91 | 73 | 87 |
| | Colon adenocarcinoma | 84 | 91 | 78 | 88 |
| | Glioma | 81 | 87 | 75 | 83 |
| | Gastrointestinal tumor | 85 | 92 | 77 | 89 |
| | Nasopharynx cancer | 86 | 93 | 78 | 92 |
| | Brain glioma | 84 | 92 | 78 | 87 |
| | Gastric cancer | 85 | 92 | 77 | 89 |
| | Lung adenocarcinoma | 82 | 91 | 73 | 87 |
| | Lung cancer | 84 | 91 | 78 | 88 |
| | Normal cells | 91 | 95 | 90 | 94 |
| Compound 46 | AML | 82 | 88 | 74 | 85 |
| | CML | 85 | 93 | 79 | 86 |
| | CLL | 82 | 88 | 76 | 89 |
| | Skin cancer | 85 | 92 | 77 | 89 |
| | Breast cancer | 82 | 89 | 76 | 86 |
| | Ovarian cancer | 79 | 88 | 72 | 81 |
| | Brain tumor | 88 | 91 | 81 | 89 |
| | Prostate cancer | 87 | 94 | 76 | 87 |
| | Head and neck squamous cell carcinomas | 84 | 91 | 78 | 88 |
| | Laryngeal cancer | 81 | 87 | 75 | 83 |
| | Pancreatic cancer | 85 | 88 | 79 | 85 |
| | Retinoblastoma | 82 | 91 | 73 | 87 |
| | Children hepatoblastoma | 84 | 91 | 78 | 88 |
| | Liver cancer | 81 | 87 | 75 | 83 |
| | Malignant melanoma | 85 | 92 | 77 | 89 |
| | Colorectal cancer | 86 | 93 | 78 | 92 |
| | Colon adenocarcinoma | 84 | 89 | 74 | 86 |
| | Glioma | 87 | 91 | 75 | 84 |
| | Gastrointestinal tumor | 82 | 89 | 76 | 86 |
| | Nasopharynx cancer | 79 | 88 | 72 | 81 |
| | Brain glioma | 88 | 91 | 81 | 89 |
| | Gastric cancer | 87 | 94 | 76 | 87 |
| | Lung adenocarcinoma | 85 | 93 | 79 | 86 |
| | Lung cancer | 82 | 88 | 76 | 89 |
| | Normal cells | 94 | 95 | 92 | 94 |
| Compound 47 | AML | 79 | 88 | 73 | 82 |
| | CML | 85 | 92 | 77 | 89 |
| | CLL | 82 | 91 | 73 | 87 |
| | Skin cancer | 84 | 91 | 78 | 88 |
| | Breast cancer | 82 | 91 | 73 | 87 |
| | Ovarian cancer | 84 | 91 | 78 | 88 |
| | Brain tumor | 81 | 87 | 75 | 83 |
| | Prostate cancer | 85 | 92 | 77 | 89 |
| | Head and neck squamous cell carcinomas | 86 | 93 | 78 | 92 |
| | Laryngeal cancer | 85 | 93 | 79 | 86 |
| | Pancreatic cancer | 84 | 91 | 78 | 88 |
| | Retinoblastoma | 81 | 87 | 75 | 83 |

TABLE 4-continued

Survival rate (%) of cancer cells, cancer stem cells and normal cells after test compound is added

| Compound | Cells | 10.0 μM Stem cells | 10.0 μM All cells (Stem cells and ordinary cells) | 20.0 μM Stem cells | 20.0 μM All cells (Stem cells and ordinary cells) |
|---|---|---|---|---|---|
| | Children hepatoblastoma | 85 | 88 | 79 | 85 |
| | Liver cancer | 82 | 91 | 73 | 87 |
| | Malignant melanoma | 82 | 89 | 76 | 86 |
| | Colorectal cancer | 79 | 88 | 72 | 81 |
| | Colon adenocarcinoma | 88 | 91 | 81 | 89 |
| | Glioma | 87 | 94 | 76 | 87 |
| | Gastrointestinal tumor | 78 | 89 | 74 | 81 |
| | Nasopharynx cancer | 82 | 88 | 74 | 85 |
| | Brain glioma | 85 | 93 | 79 | 86 |
| | Gastric cancer | 82 | 88 | 76 | 89 |
| | Lung adenocarcinoma | 85 | 92 | 77 | 89 |
| | Lung cancer | 85 | 93 | 79 | 86 |
| | Normal cells | 93 | 95 | 92 | 94 |
| Compound 48 | AML | 47 | 59 | 38 | 48 |
| | CML | 51 | 69 | 46 | 51 |
| | CLL | 46 | 67 | 38 | 48 |
| | Skin cancer | 46 | 62 | 39 | 47 |
| | Breast cancer | 54 | 76 | 47 | 58 |
| | Ovarian cancer | 56 | 68 | 45 | 61 |
| | Brain tumor | 66 | 78 | 53 | 69 |
| | Prostate cancer | 62 | 75 | 51 | 62 |
| | Head and neck squamous cell carcinomas | 64 | 73 | 58 | 68 |
| | Laryngeal cancer | 63 | 76 | 55 | 66 |
| | Pancreatic cancer | 55 | 68 | 49 | 62 |
| | Retinoblastoma | 62 | 82 | 54 | 69 |
| | Children hepatoblastoma | 68 | 75 | 56 | 68 |
| | Liver cancer | 74 | 82 | 61 | 73 |
| | Malignant melanoma | 82 | 88 | 76 | 86 |
| | Colorectal cancer | 66 | 79 | 55 | 67 |
| | Colon adenocarcinoma | 58 | 66 | 49 | 56 |
| | Glioma | 69 | 78 | 60 | 74 |
| | Gastrointestinal tumor | 57 | 73 | 52 | 62 |
| | Nasopharynx cancer | 57 | 64 | 48 | 59 |
| | Brain glioma | 52 | 66 | 43 | 54 |
| | Gastric cancer | 51 | 66 | 39 | 48 |
| | Lung adenocarcinoma | 67 | 77 | 55 | 64 |
| | Lung cancer | 61 | 72 | 54 | 67 |
| | Normal cells | 91 | 92 | 89 | 91 |
| Compound 49 | AML | 85 | 92 | 77 | 89 |
| | CML | 87 | 90 | 76 | 86 |
| | CLL | 82 | 91 | 74 | 85 |
| | Skin cancer | 85 | 93 | 79 | 86 |
| | Breast cancer | 82 | 89 | 79 | 87 |
| | Ovarian cancer | 86 | 93 | 76 | 88 |
| | Brain tumor | 83 | 88 | 79 | 87 |
| | Prostate cancer | 85 | 92 | 77 | 89 |
| | Head and neck squamous cell carcinomas | 82 | 91 | 73 | 87 |
| | Laryngeal cancer | 84 | 91 | 78 | 88 |
| | Pancreatic cancer | 81 | 87 | 75 | 83 |
| | Retinoblastoma | 85 | 92 | 77 | 89 |
| | Children hepatoblastoma | 86 | 93 | 78 | 92 |
| | Liver cancer | 85 | 93 | 79 | 86 |
| | Malignant melanoma | 82 | 88 | 79 | 87 |
| | Colorectal cancer | 82 | 88 | 74 | 85 |
| | Colon adenocarcinoma | 85 | 93 | 79 | 86 |
| | Glioma | 82 | 88 | 76 | 89 |
| | Gastrointestinal tumor | 85 | 92 | 77 | 89 |
| | Nasopharynx cancer | 84 | 93 | 77 | 86 |
| | Brain glioma | 83 | 88 | 79 | 87 |
| | Gastric cancer | 85 | 92 | 77 | 89 |
| | Lung adenocarcinoma | 84 | 91 | 78 | 88 |
| | Lung cancer | 79 | 88 | 73 | 82 |
| | Normal cells | 94 | 96 | 92 | 95 |
| Compound 50 | AML | 45 | 57 | 36 | 47 |
| | CML | 57 | 64 | 46 | 58 |
| | CLL | 47 | 58 | 36 | 47 |
| | Skin cancer | 57 | 66 | 43 | 58 |
| | Breast cancer | 64 | 75 | 52 | 65 |
| | Ovarian cancer | 62 | 77 | 55 | 67 |
| | Brain tumor | 62 | 72 | 54 | 63 |
| | Prostate cancer | 54 | 66 | 41 | 54 |
| | Head and neck squamous cell carcinomas | 56 | 67 | 47 | 58 |
| | Laryngeal cancer | 64 | 75 | 53 | 64 |
| | Pancreatic cancer | 53 | 64 | 43 | 49 |
| | Retinoblastoma | 54 | 65 | 44 | 53 |
| | Children hepatoblastoma | 42 | 55 | 34 | 47 |
| | Liver cancer | 53 | 66 | 46 | 54 |
| | Malignant melanoma | 64 | 82 | 54 | 66 |
| | Colorectal cancer | 64 | 76 | 55 | 66 |
| | Colon adenocarcinoma | 43 | 55 | 35 | 49 |
| | Glioma | 62 | 74 | 45 | 56 |
| | Gastrointestinal tumor | 55 | 64 | 44 | 53 |
| | Nasopharynx cancer | 44 | 54 | 37 | 48 |
| | Brain glioma | 63 | 74 | 47 | 58 |
| | Gastric cancer | 45 | 54 | 37 | 48 |
| | Lung adenocarcinoma | 46 | 57 | 36 | 47 |
| | Lung cancer | 43 | 54 | 33 | 47 |
| | Normal cells | 90 | 92 | 89 | 91 |

Embodiment 4: Injection

Respectively dissolve Compounds 1-50 prepared in Embodiment 1 with a few amount of DMSO and then add water for injection as normal, filter precisely, charge and seal before sterilize them to prepare into injection.

Embodiment 5: Tablet

Add excipient with a ratio of 5:1 by weight between Compounds 1-50 prepared in Embodiment 1 and excipient. Pellitize and tablet it to make tablet.

Embodiment 6: Capsule

Add excipient with a ratio of 5:1 by weight between Compounds 1-50 prepared in Embodiment 1 and excipient. Pellitize and tablet it to make capsule.

The compounds, uses and methods according to the present invention have been described in the specific embodiments as above. Those skilled in the art can refer to the contents of the present invention to appropriately modify the factors such as raw materials or process conditions to realize other corresponding purposes. Nevertheless, no related changes shall break away from the contents of the present invention and all the similar substitutions and changes are obvious to those skilled in the art and shall be deemed within the scope of the present invention.

What is claimed is:
1. A method of treating rheumatoid arthritis in a patient comprising administering a therapeutically effective amount of compound of formula I
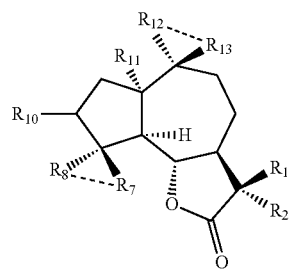
Formula (I) to a patient in need of rheumatoid arthritis treatment wherein the compounds of Formula I are selected from the group consisting of
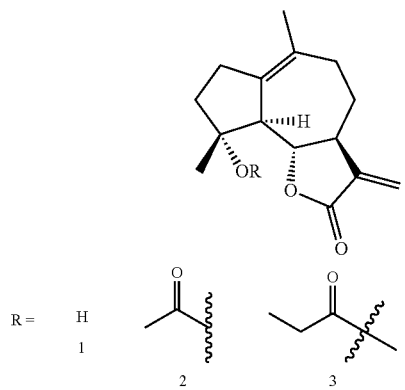
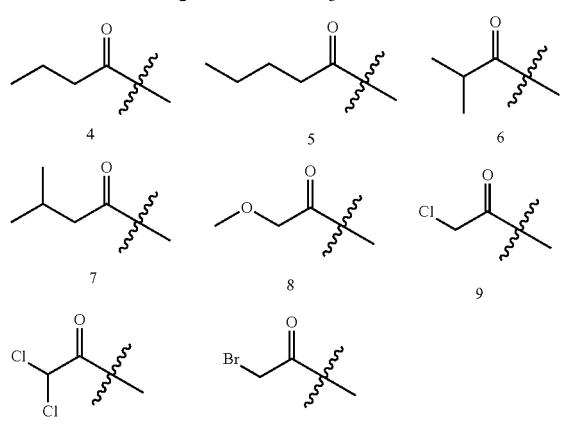
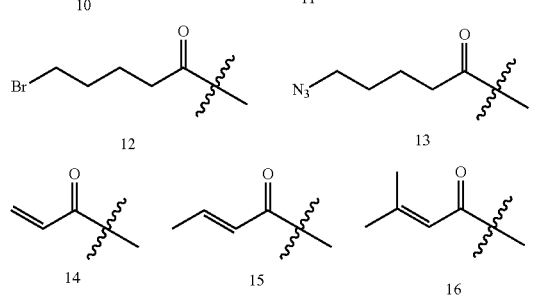
-continued
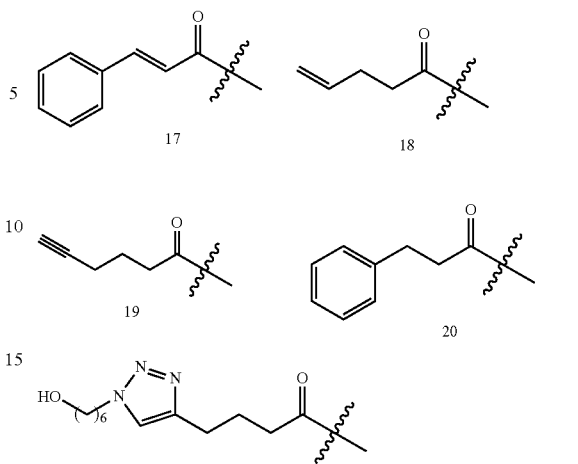
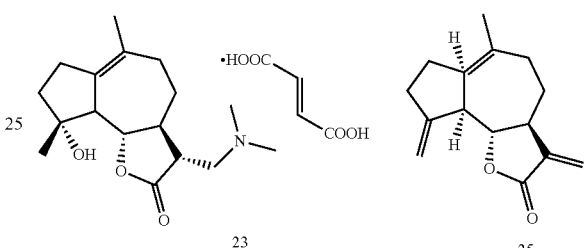
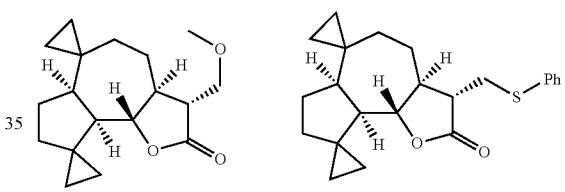
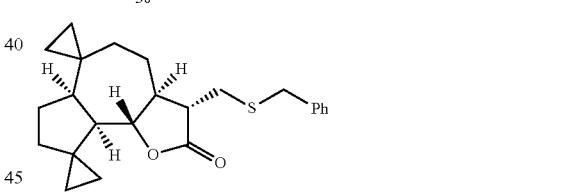
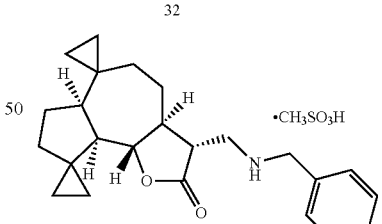
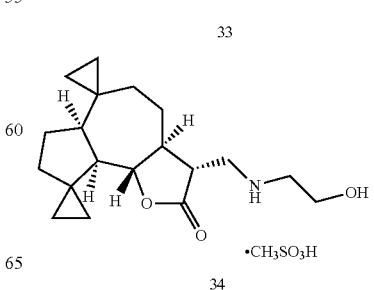

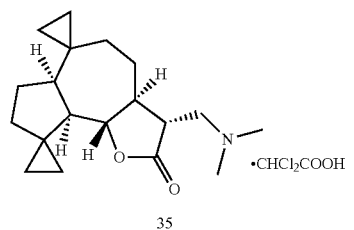
35
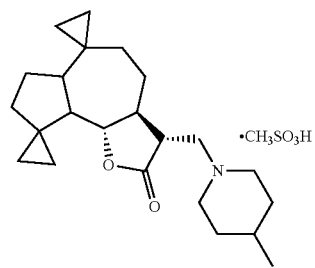
36
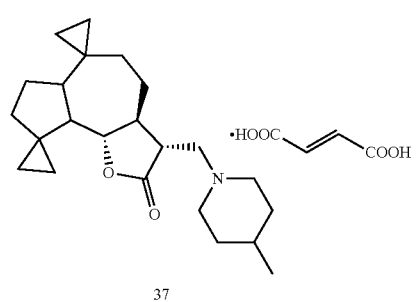
37
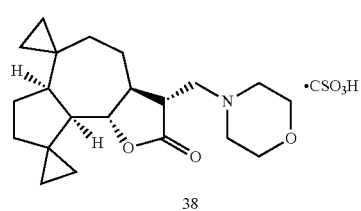
38
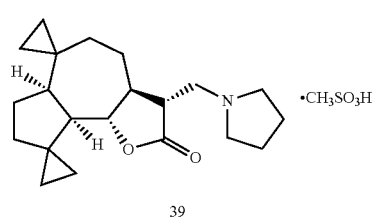
39
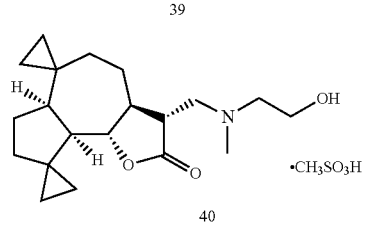
40
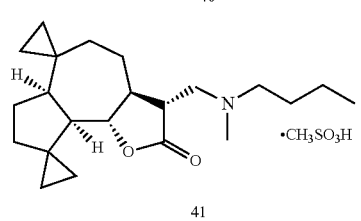
41
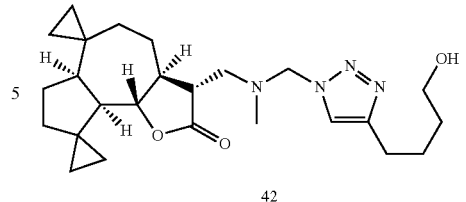
42
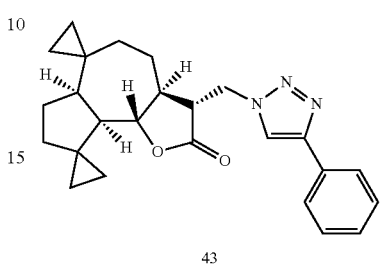
43
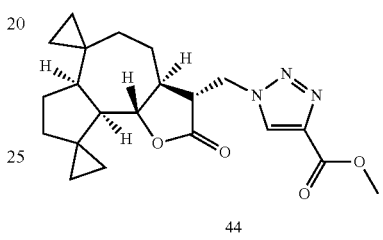
44
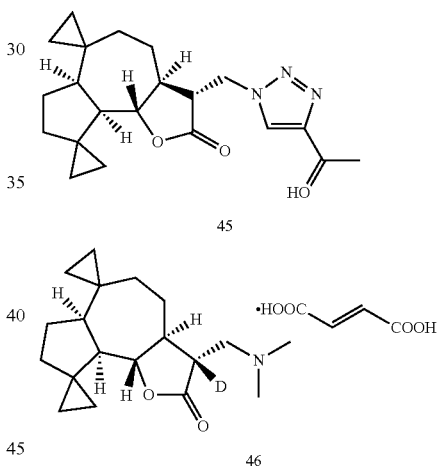
45
46
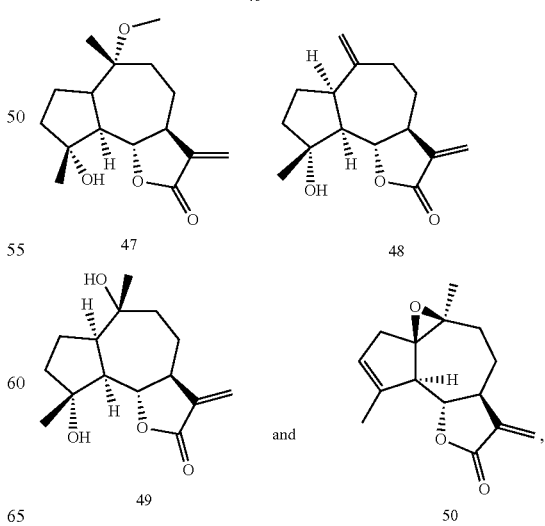
47
48
49
and
50 and wherein the compound of formula (I) are formulated in the form of injections, tablet, or capsule and administered in a therapeutically effective amount to reduce a content of TNF-α, PGE2 and IL-1β.

* * * * *